(12) United States Patent
Thompson et al.

(10) Patent No.: US 8,822,042 B2
(45) Date of Patent: Sep. 2, 2014

(54) LUMINESCENT CYCLOMETALLATED IRIDIUM(III) COMPLEXES HAVING ACETYLIDE LIGANDS

(75) Inventors: Mark E. Thompson, Anaheim, CA (US); Alberto Bossi, Gallorate (IT); Peter Ivan Djurovich, Los Angeles, CA (US)

(73) Assignee: The University of Southern California, Los Angeles, CA (US)

( * ) Notice: Subject to any disclaimer, the term of this patent is extended or adjusted under 35 U.S.C. 154(b) by 500 days.

(21) Appl. No.: 13/161,296

(22) Filed: Jun. 15, 2011

(65) Prior Publication Data

US 2012/0007061 A1 Jan. 12, 2012

Related U.S. Application Data

(60) Provisional application No. 61/359,118, filed on Jun. 28, 2010.

(51) Int. Cl.
| | |
|---|---|
| *C09K 11/06* | (2006.01) |
| *H01L 51/00* | (2006.01) |
| *C07F 15/00* | (2006.01) |
| *H01L 51/54* | (2006.01) |
| *H01L 51/50* | (2006.01) |

(52) U.S. Cl.
CPC .... *H01L 51/0085* (2013.01); *C09K 2211/1044* (2013.01); *C09K 2211/185* (2013.01); *C09K 2211/1029* (2013.01); *C07F 15/0033* (2013.01); *H01L 51/5016* (2013.01); *Y10S 428/917* (2013.01)

USPC .......... 428/690; 428/917; 313/504; 313/506; 252/301.16; 257/40; 257/E51.044; 546/4; 546/10; 548/103; 548/108

(58) Field of Classification Search
None
See application file for complete search history.

(56) References Cited

U.S. PATENT DOCUMENTS

| | | | |
|---|---|---|---|
| 2005/0112406 A1* | 5/2005 | Han et al. ...................... | 428/690 |
| 2006/0115675 A1* | 6/2006 | Haga et al. .................... | 428/690 |
| 2007/0141398 A1* | 6/2007 | Okuda .......................... | 428/690 |

OTHER PUBLICATIONS

Liu et al. "Theoretical studies on structures and spectroscopic properties of a series of novel mixed-ligand Ir(III) complexes [Ir(Mebib)(ppy)X]" Dalton Trans. 2007. pp. 1922-1928.*

* cited by examiner

*Primary Examiner* — Michael H Wilson
(74) *Attorney, Agent, or Firm* — Morgan, Lewis & Bockius LLP

(57) ABSTRACT

The present invention relates to phosphorescent (triplet-emitting) organometallic materials. The phosphorescent materials of the present invention comprise Ir(III)cyclometallated alkynyl complexes for use as triplet light-emitting materials. The Ir(III)cyclometallated alkynyl complexes comprise at least one cyclometallating ligand and at least one alkynyl ligand bonded to the iridium. Also provided is an organic light emitting device comprising an anode, a cathode and an emissive layer between the anode and the cathode, wherein the emissive layer comprises a Ir(III)cyclometallated alkynyl complex as a triplet emitting material.

3 Claims, 23 Drawing Sheets

Ir(ppz)₂(CN*t*Bu)(CCPh)

Figure 3: LCMS, C18, acetonitrile:H₂O, 80:20 to 90:10; ESI+, [M+H]⁺ 664.4

Figure 5: LCMS, C18, acetonitrile:H$_2$O, 80:20 to 90:10; ESI+, [M+H]$^+$ 686.4

Ir(ppy)$_2$(CN$t$Bu)(CCPheneatr)

Figure 7: LCMS, C18, acetonitrile:H$_2$O, 80:20 to 90:10; ESI+, [M+H]$^+$ 786.5

Ir(ppy)$_2$(CCPh)$_2$Li .

Ir(ppz)₂(CN*t*Bu)(CCPhenantr)

LUMINESCENT CYCLOMETALLATED IRIDIUM(III) COMPLEXES HAVING ACETYLIDE LIGANDS

REFERENCE TO RELATED APPLICATIONS

This application claims priority to U.S. Provisional Application No. 61/359,118, filed Jun. 28, 2010, the content of which is incorporated herein by reference in its entirety.

GOVERNMENT RIGHTS

The present invention was made under Department of Energy Grant No. DE-FC26-08NT01585. The government may have certain rights to the subject invention.

RESEARCH AGREEMENTS

The claimed invention was made by, on behalf of, and/or in connection with one or more of the following parties to a joint university corporation research agreement: Regents of the University of Michigan, Princeton University, the University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to phosphorescent (triplet-emitting) organometallic materials. The phosphorescent materials of the present invention comprise Ir(III)cyclometallated alkynyl systems for use as triplet emitting dopants in organic light emitting diodes (OLEDs), contrast agent, oxygen sensing and related applications.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

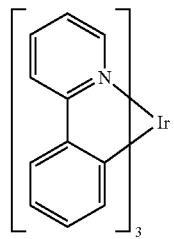

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material or organometallic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Phosphorescent (triplet-emitting) organometallic materials are provided. The phosphorescent materials of the present invention comprise Ir(III)cyclometallated alkynyl systems for use as triplet emitting dopants in organic light emitting diodes (OLEDs), contrast agent, oxygen sensing and related applications.

In preferred aspects of the invention, the triplet-emitting material is a compound having the formula I:

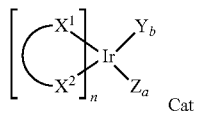

wherein:
$X^1 \wedge X^2$ is a substituted or unsubstituted bidentate cyclometallated aromatic ligand;
$X^1$ and $X^2$ are independently selected from C and N;
Z is an acetylide ligand having the structure:

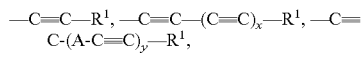

each $R^1$ is independently selected from the group consisting of H, alkyl, cycloalkyl, alkenyl, cycloalkenyl, aryl, heteroaryl, $Si(R^2)_3$, $M(L)_z$, and a heterocyclic group, each of which may be substituted or unsubstituted;
each x is independently selected from 0-5;
each y is independently selected from 0-5;
each $R^2$ is independently selected from H, alkyl, cycloalkyl, alkenyl, cycloalkenyl, aryl, heteroaryl, and a heterocyclic group;
M is a metal atom;
L is a mono-, bi- or tridentate ligand;
z is 0-5;
A is aryl or heteroaryl;
Y is a monodentate ancillary ligand;
additionally or alternatively, X and Y, two X ligands, and/or two Y ligands may be connected by a bridging moiety;
a is 1, 2, 3, or 4;
b is 0, 1, 2, or 3;
n is 1 or 2;
the sum of a+b+n is 4 or 5; and
Cat is an optional cation the charge of which provides a net neutral charge for formula I.

Also provided is an organic light emitting device comprising an anode, a cathode and an emissive layer between the anode and the cathode, wherein the emissive layer comprises a compound of the formula I.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
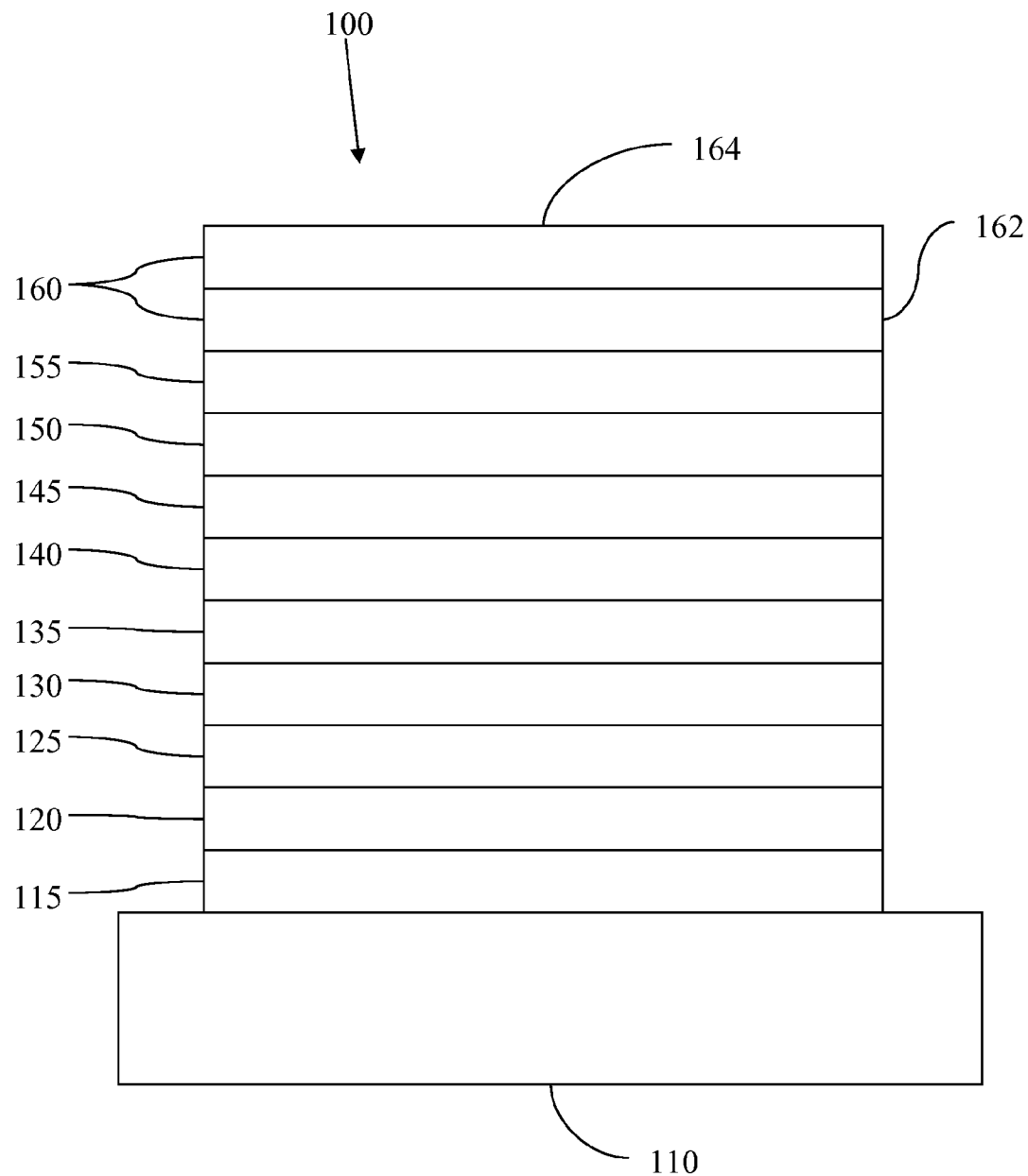
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
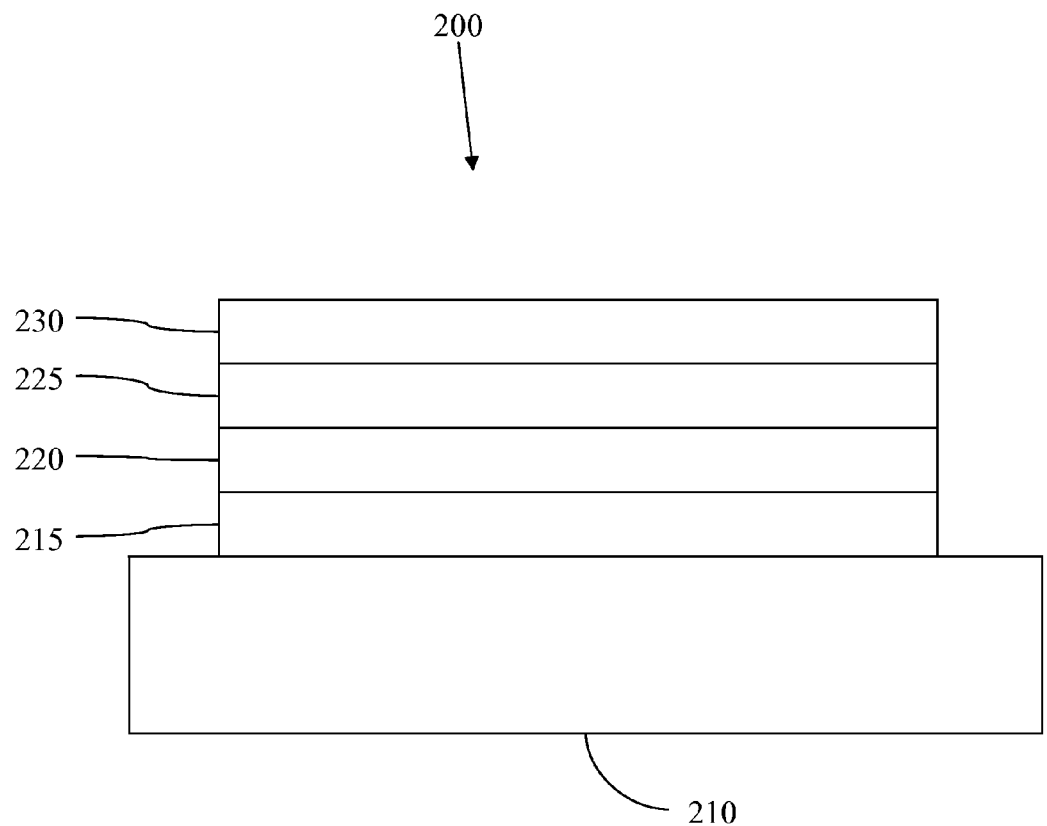
FIG. 2 shows an inverted organic light emitting device that does not have a separate electron transport layer.
Figure 3:
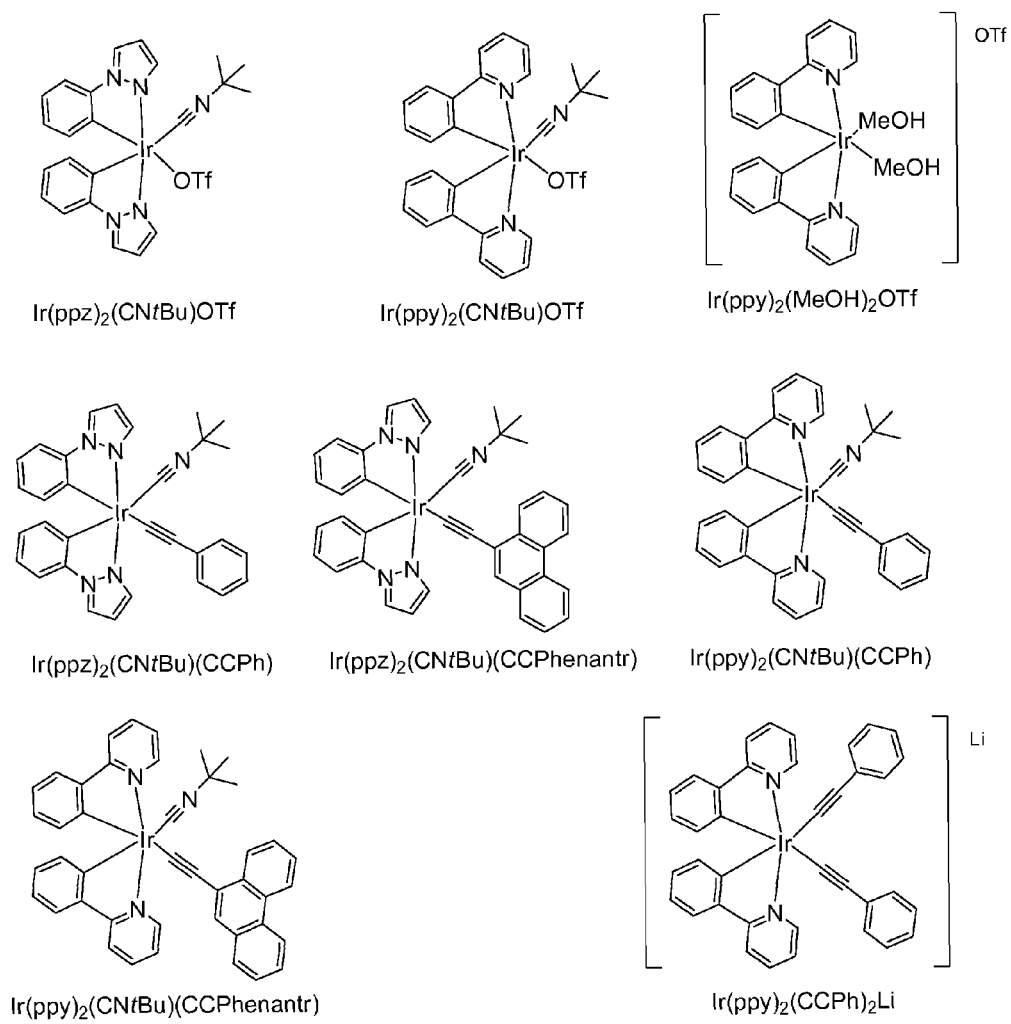
FIG. 3 shows the chemical structures of Iridium (III) complexes with labels.
Figure 4:
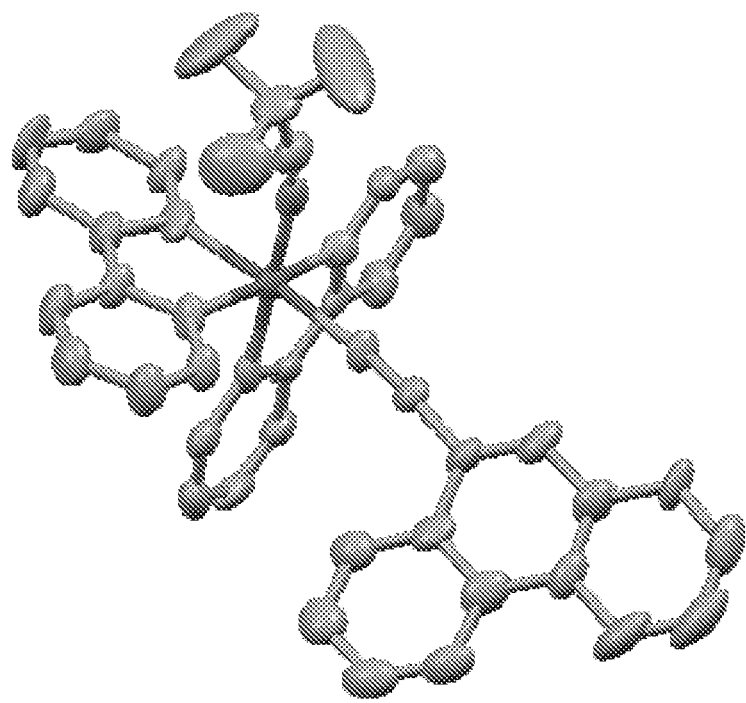
FIG. 4 shows the X-ray crystal structure of $Ir(ppy)_2$(CNtBu)(CCPheneatr) (ORTEP view).
Figure 5:
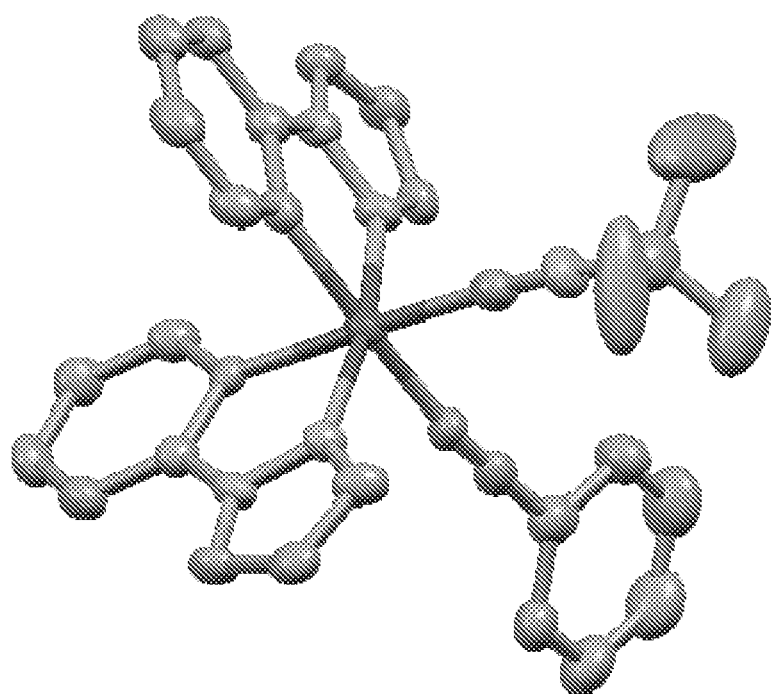
FIG. 5 shows the X-ray crystal structure of $Ir(ppz)_2$(CNtBu)(CCPh) (ORTEP view).
Figure 6:
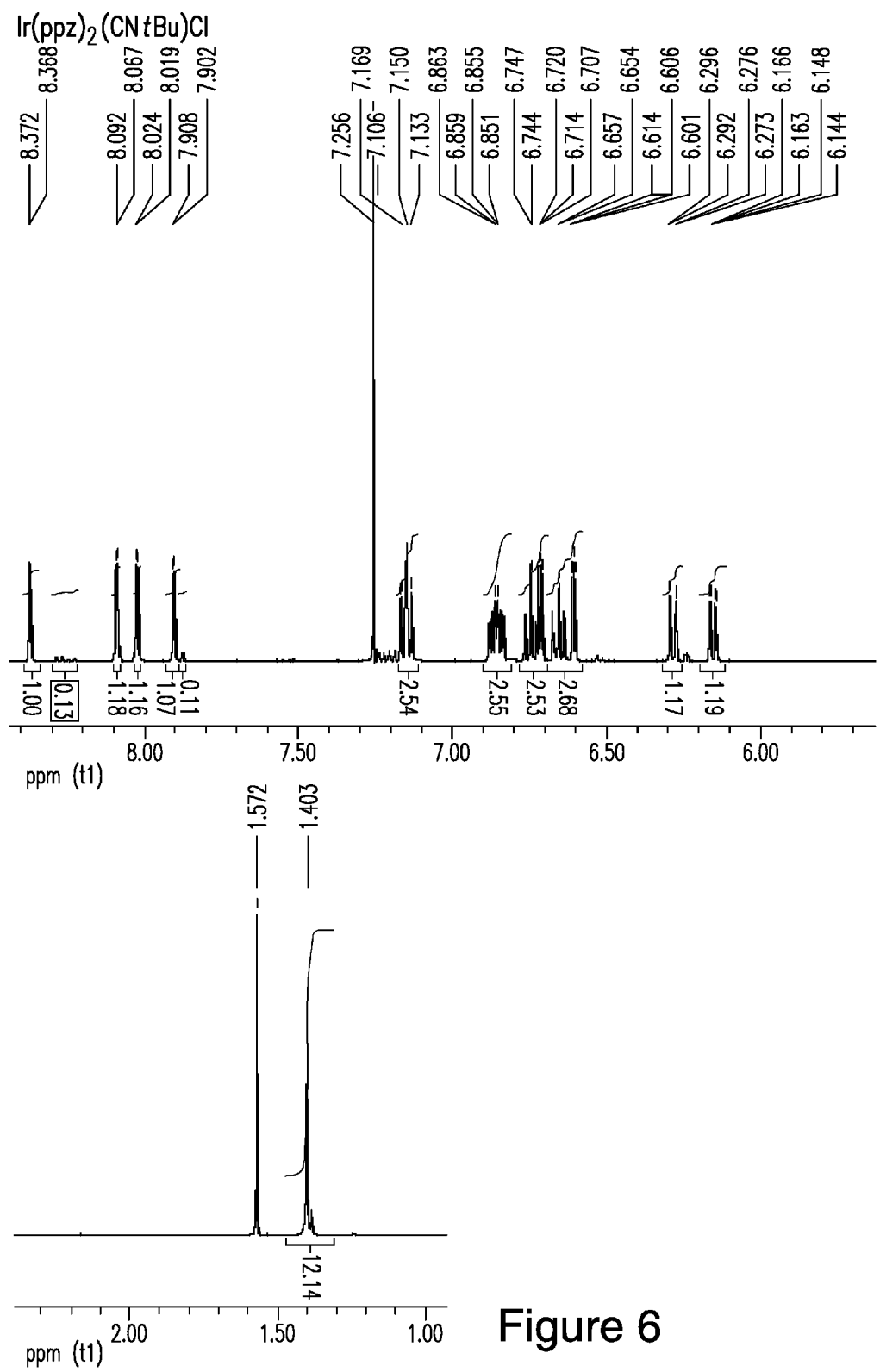
FIG. 6 shows the $^1$H NMR (400 MHz, $CDCl_3$, ppm) for $Ir(ppz)_2$(CNtBu)Cl.
Figure 7:
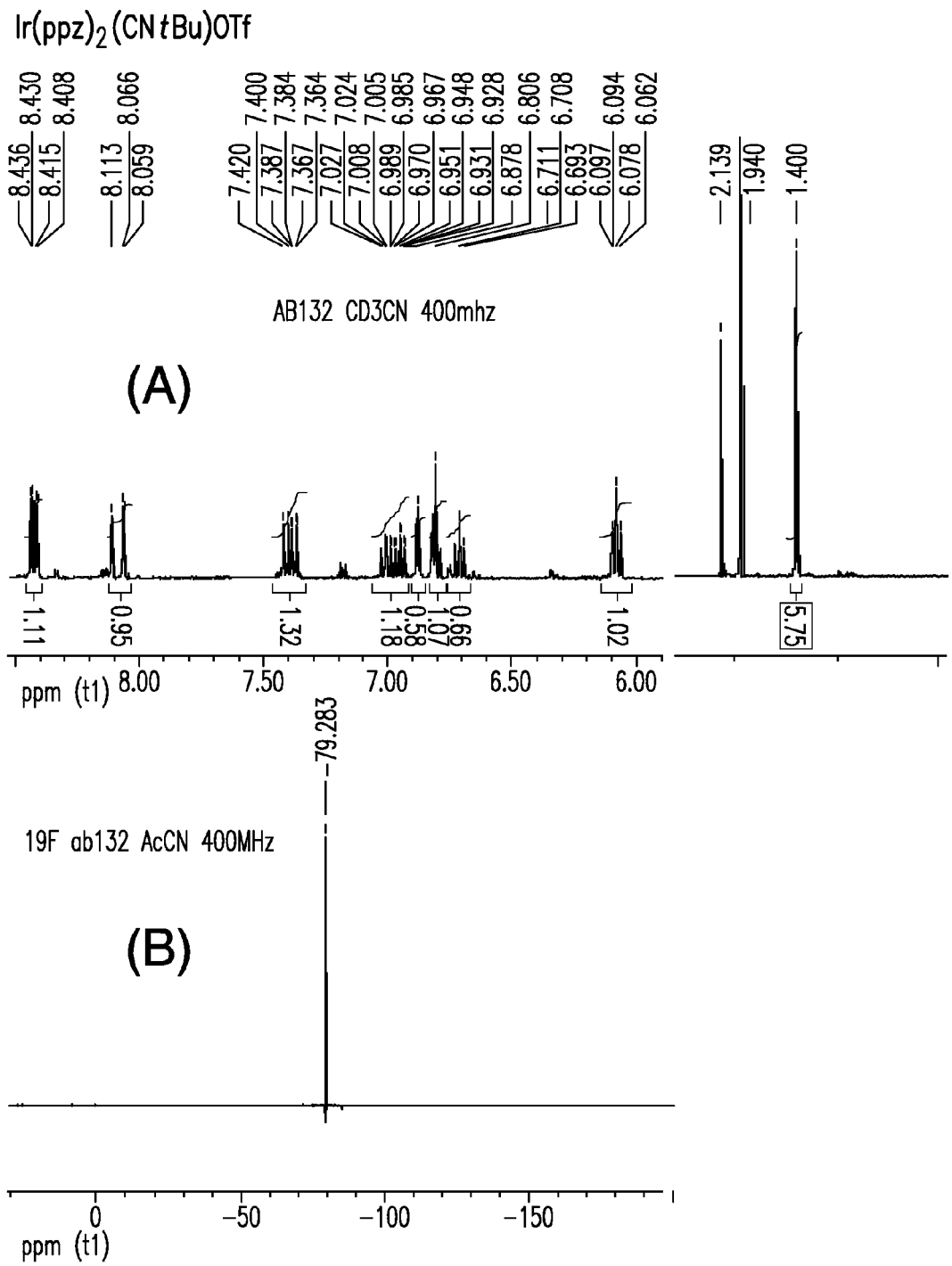
FIG. 7 shows the $^1$H NMR (400 MHz, $CD_3CN$, ppm) (A) and the $^{19}$F NMR (376 MHz, $CD_3CN$, ppm) (B) for $Ir(ppz)_2$(CNtBu)OTf.
Figure 8:
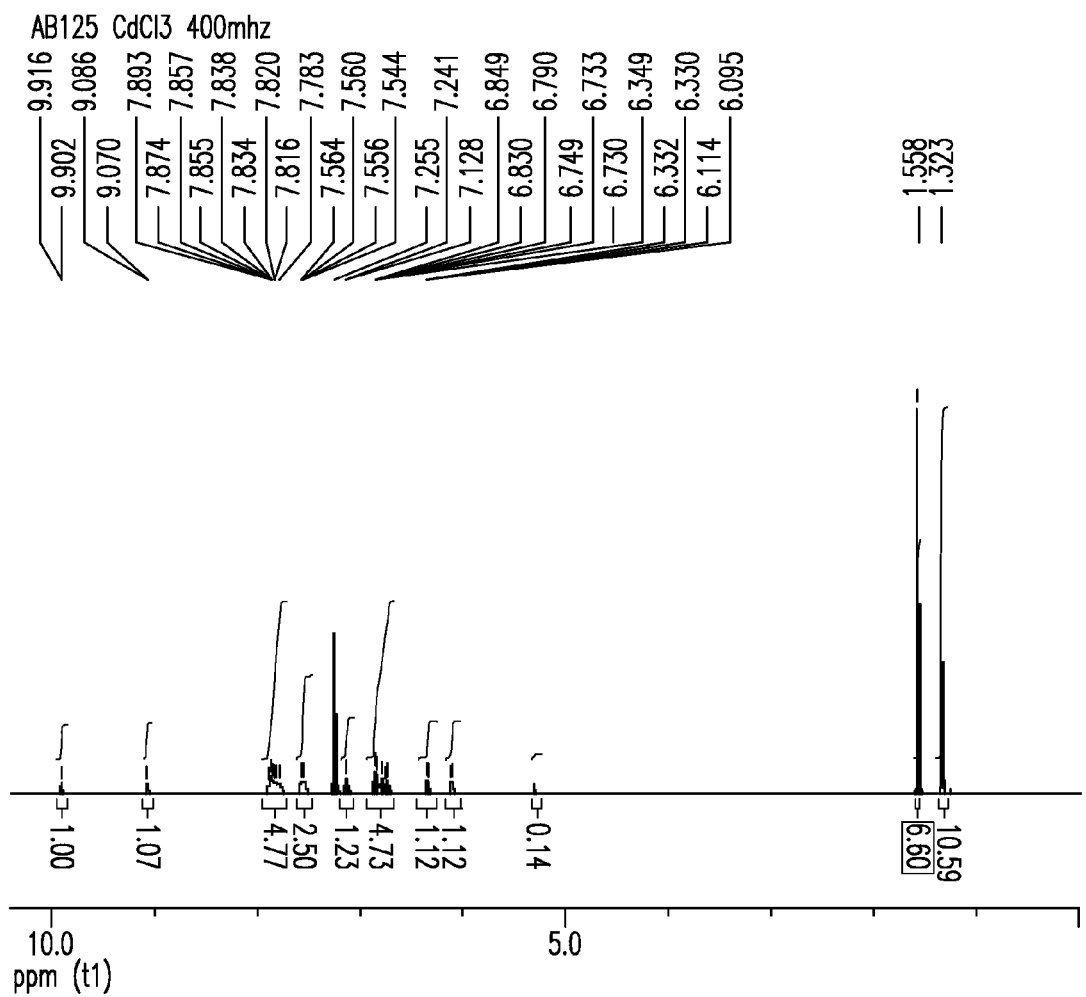
FIG. 8 shows the $^1$H NMR (400 MHz, $CDCl_3$, ppm) for $Ir(ppy)_2$(CNtBu)Cl.
Figure 9:
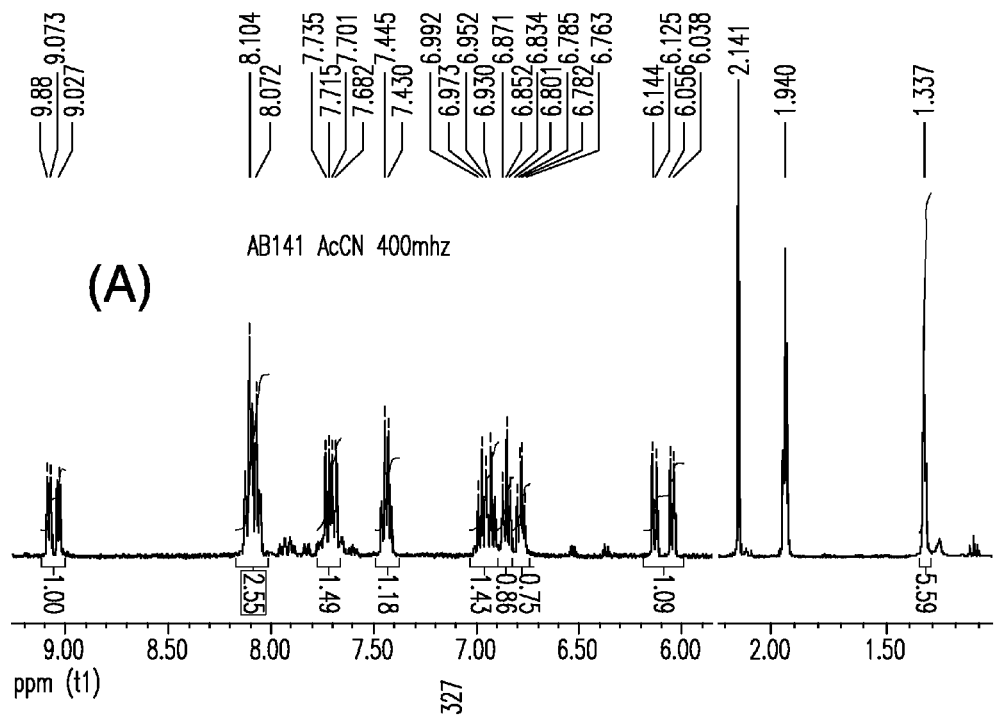
FIG. 9 shows the $^1$H NMR (400 MHz, $CD_3CN$, ppm) (A) and the $^{19}$F NMR (376 MHz, $CD_3CN$, ppm) for $Ir(ppy)_2$(CNtBu)OTf.
Figure 9:
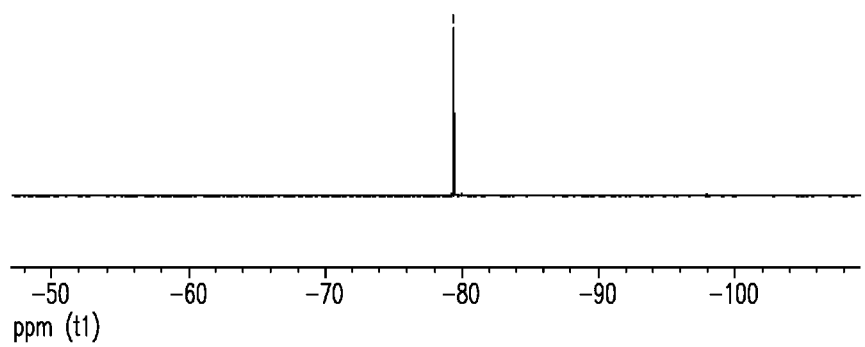
Figure 10:
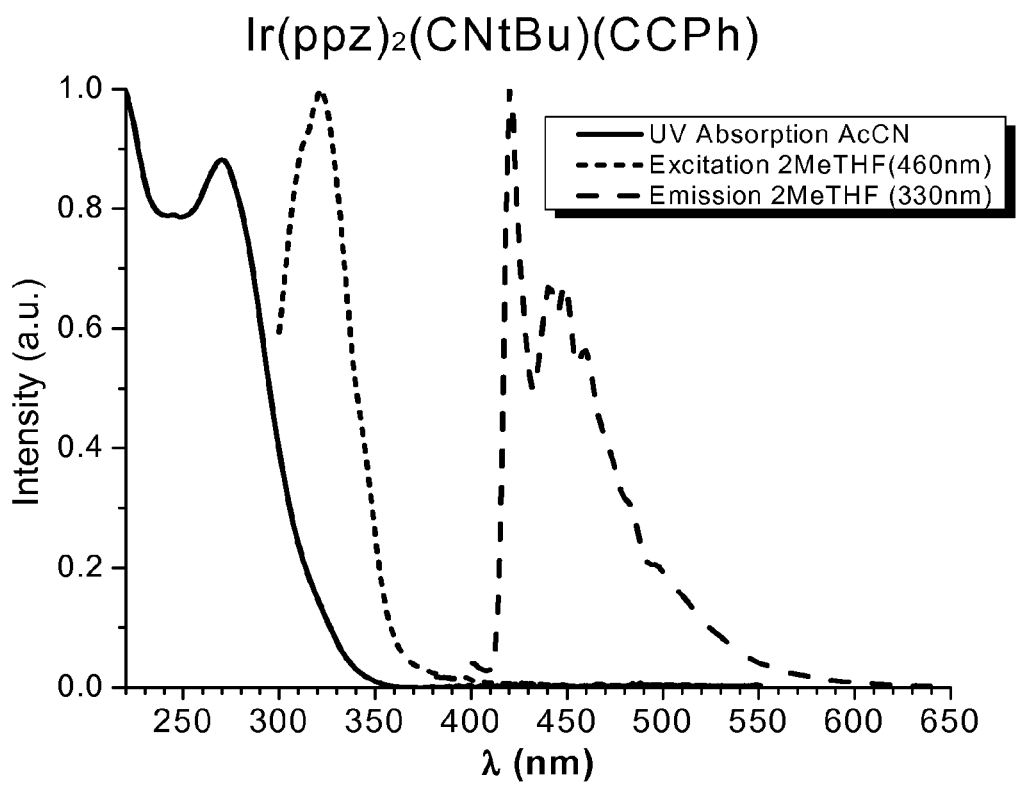
FIG. 10 shows absorption (acetonitrile), excitation and emission (2MeTHF, 77K) spectra of $Ir(ppz)_2$(CNtBu)(CCPh).
Figure 11:
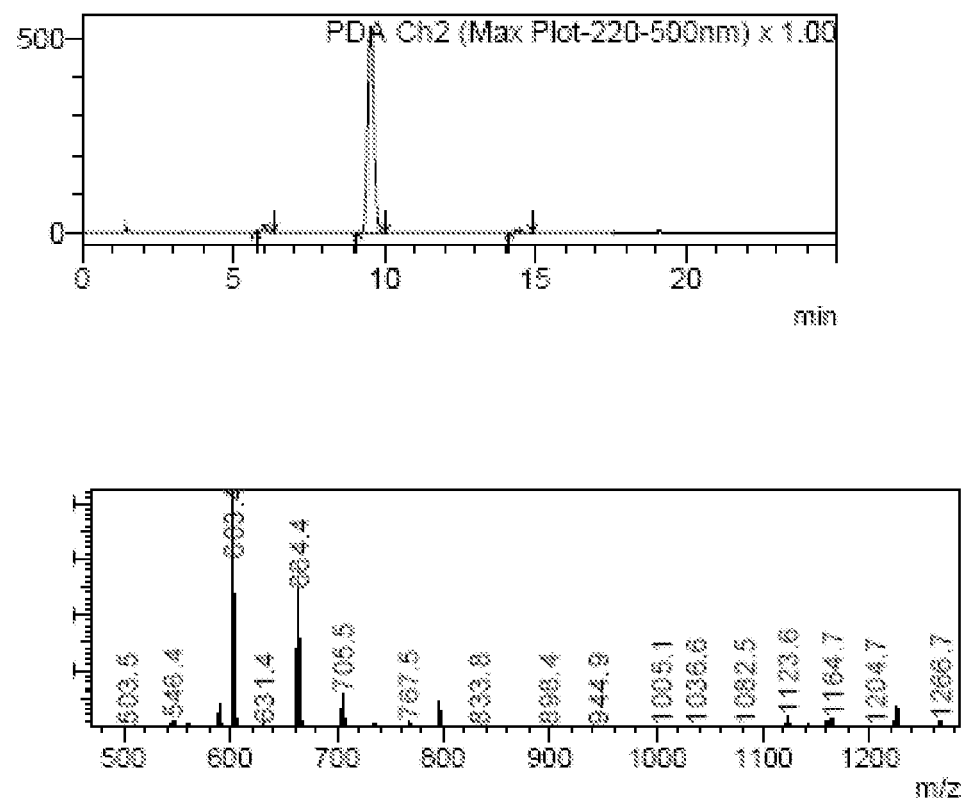
FIG. 11 shows the LCMS (C18, acetonitrile:$H_2O$, 80:20 to 90:10; ESI+) for $Ir(ppz)_2$(CNtBu)(CCPh).
Figure 12:
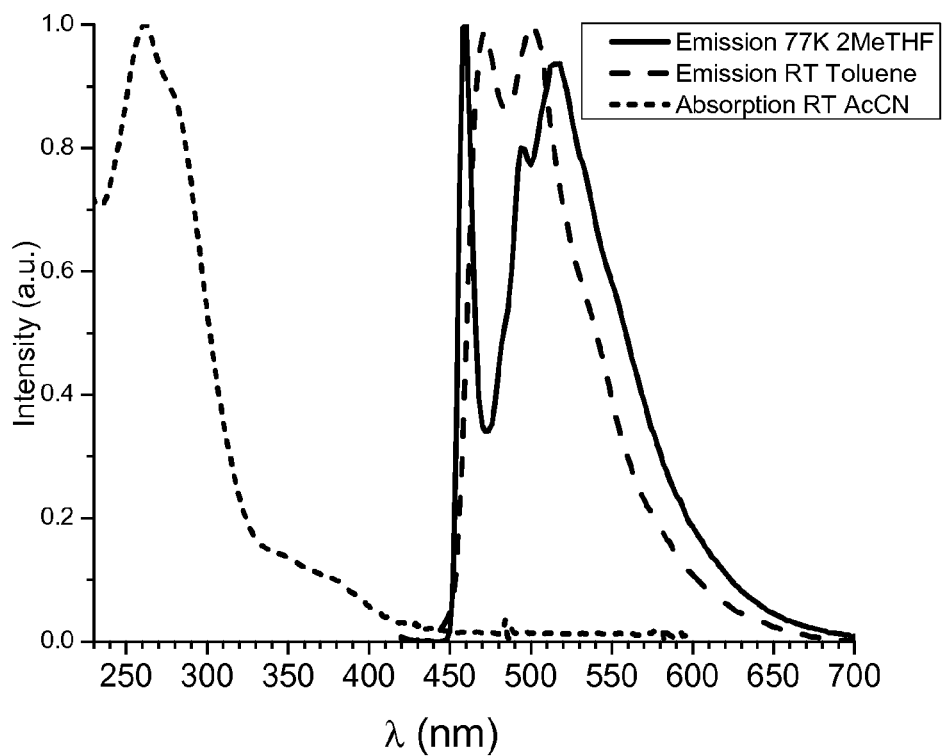
FIG. 12 shows the absorption (acetonitrile) and emission (toluene, room temperature; 2MeTHF, 77K) spectra of $Ir(ppz)_2$(CNtBu)(CCPh).
Figure 13:
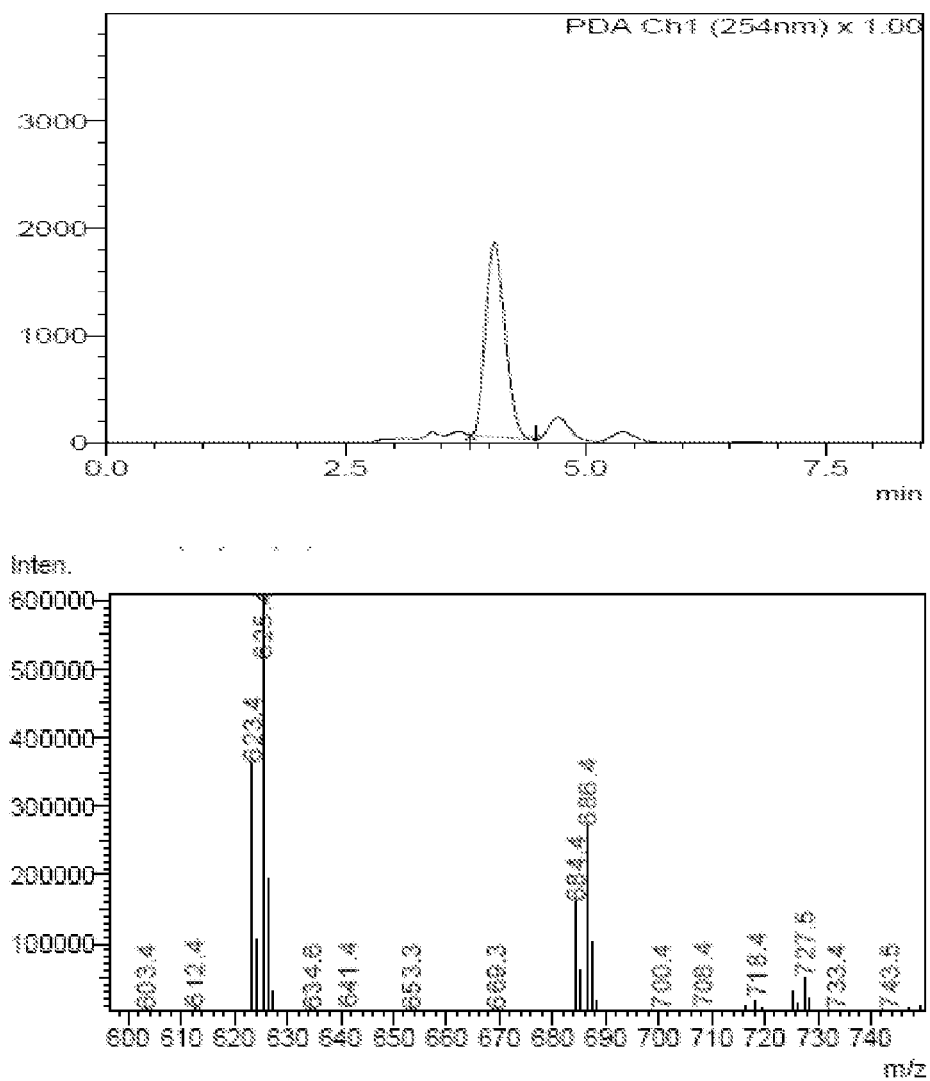
FIG. 13 shows the LCMS (C18, acetonitrile:$H_2O$, 80:20 to 90:10; ESI+) for $Ir(ppy)_2$(CNtBu)(CCPh).
Figure 14:
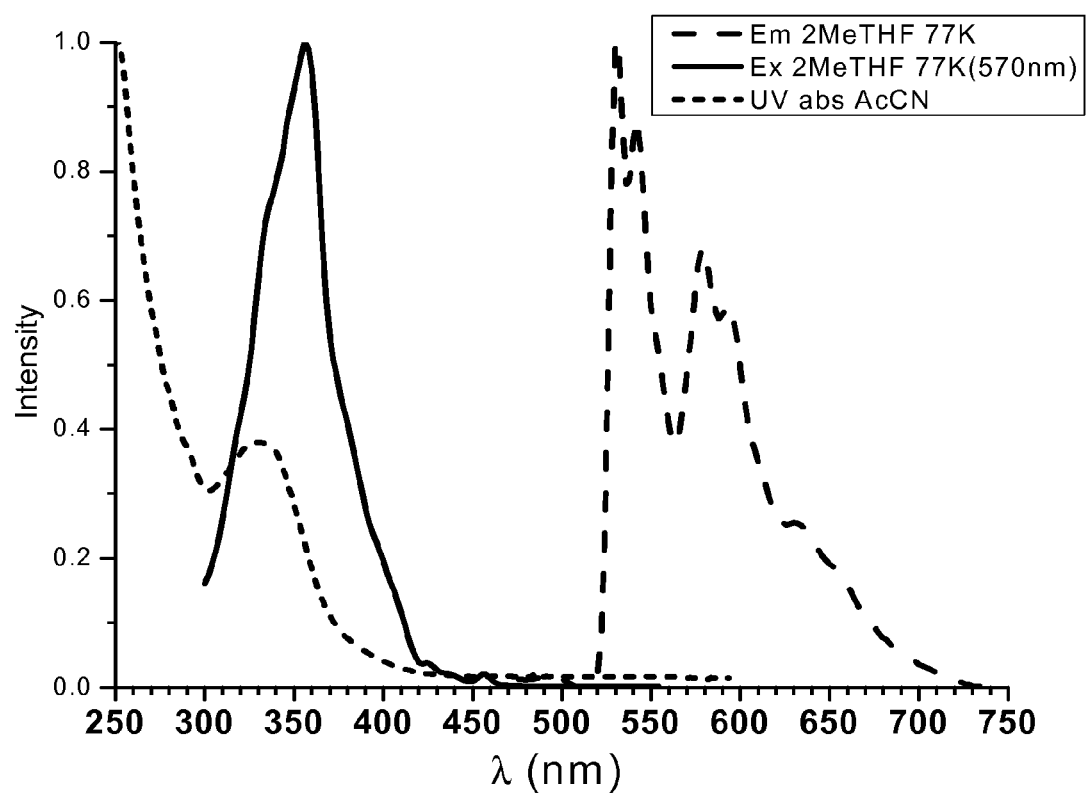
FIG. 14 shows absorption (acetonitrile), excitation and emission (2MeTHF, 77K) spectra of $Ir(ppy)_2$(CNtBu)(CCPheneatr).
Figure 15:
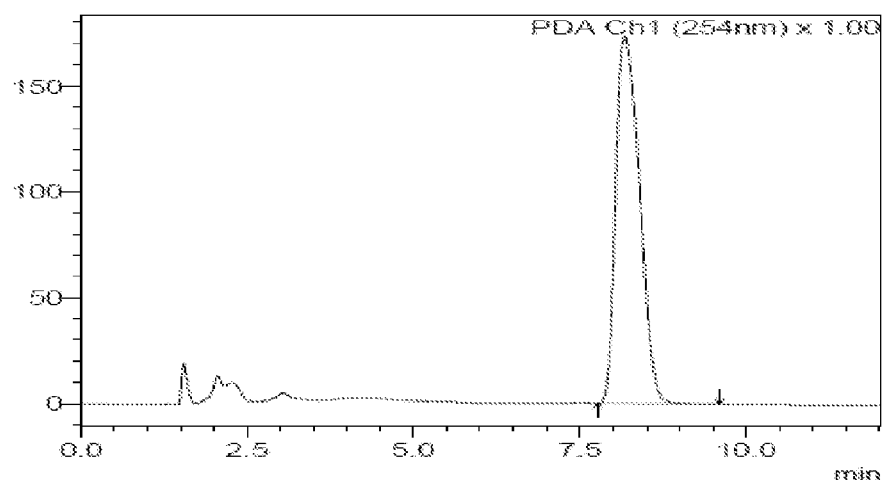
FIG. 15 shows the LCMS (C18, acetonitrile:$H_2O$, 80:20 to 90:10; ESI+) of $Ir(ppy)_2$(CNtBu)(CCPheneatr).
Figure 15:
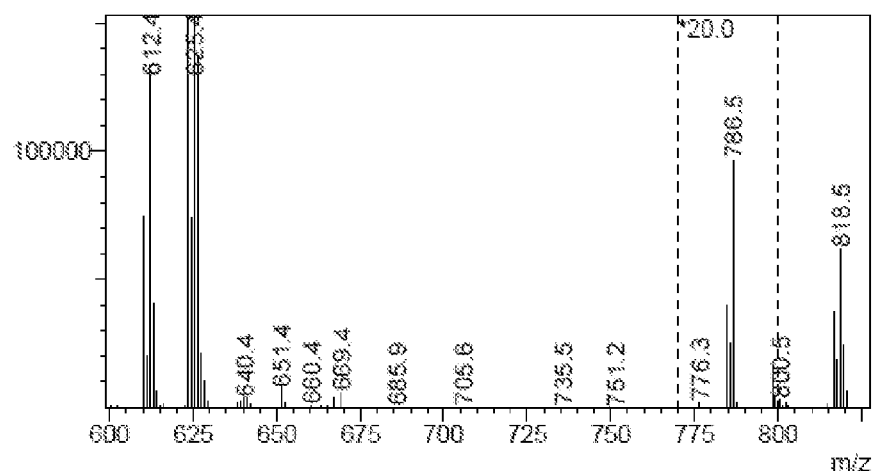
Figure 16:
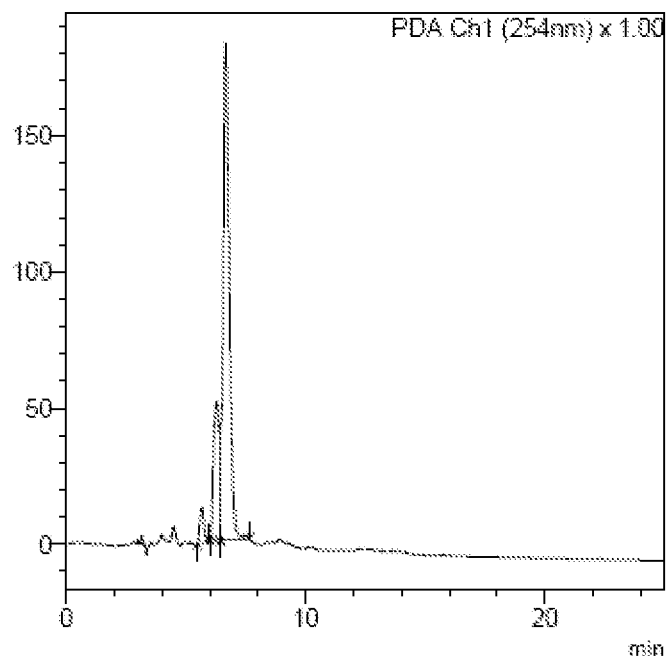
FIG. 16 shows the LCMS (C18, acetonitrile:$H_2O$, 80:20 to 90:10; ESI+,−) for $Ir(ppy)_2$(CCPh)$_2$Li.
Figure 16:
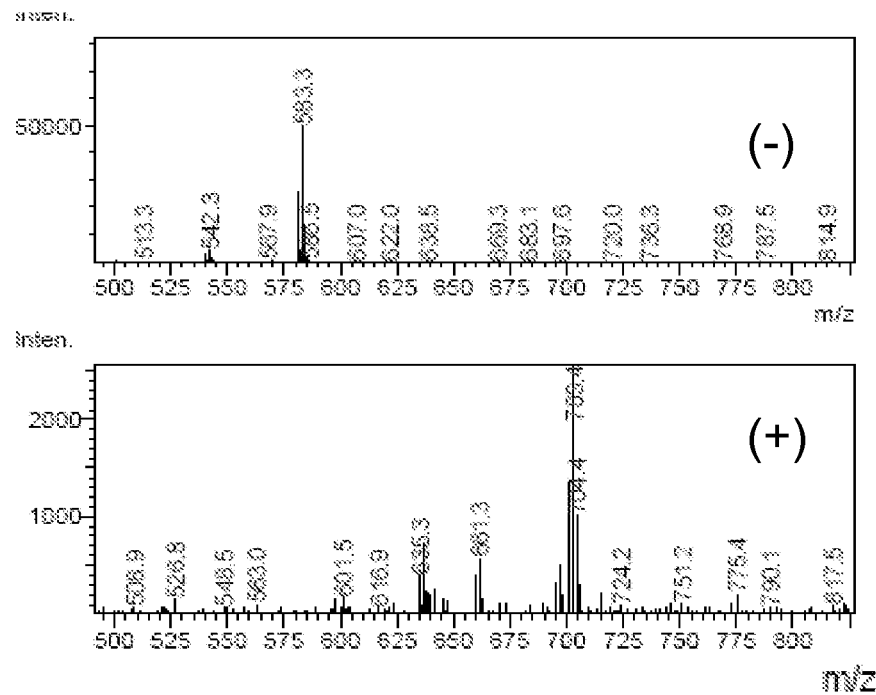
Figure 17:
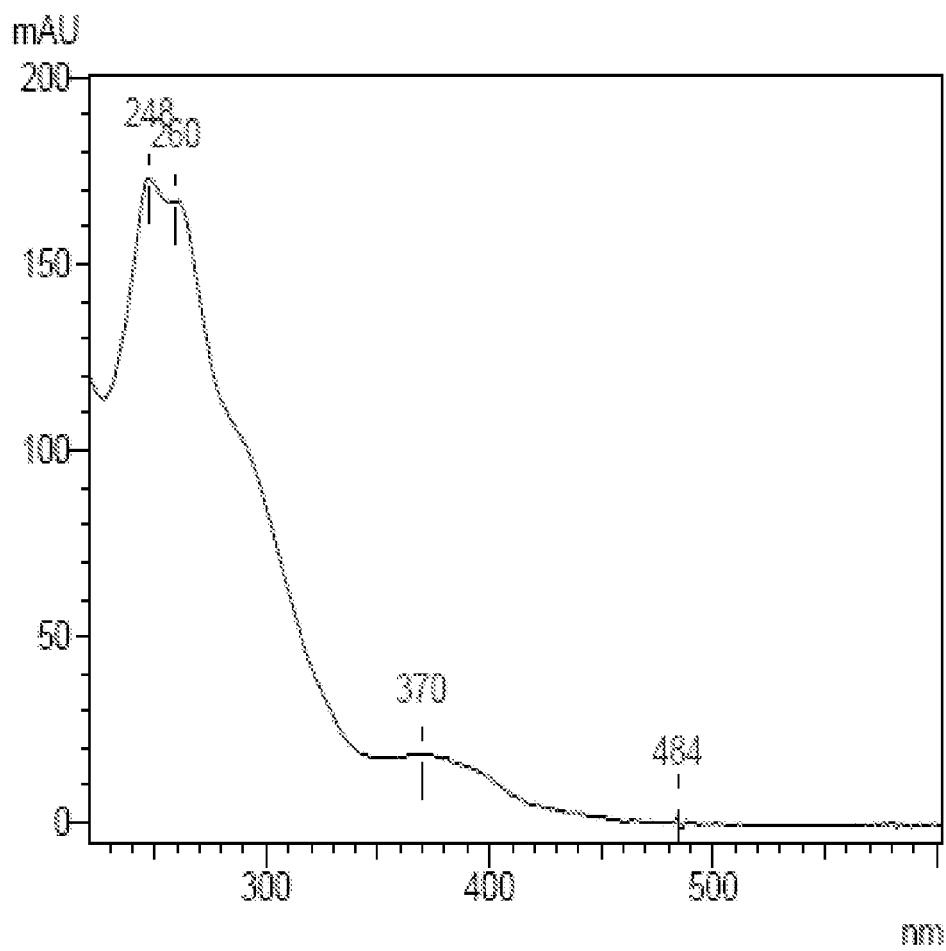
FIG. 17 shows the UV Absorption (Acetonitrile) of $Ir(ppy)_2$(CCPh)$_2$Li.
Figure 18:
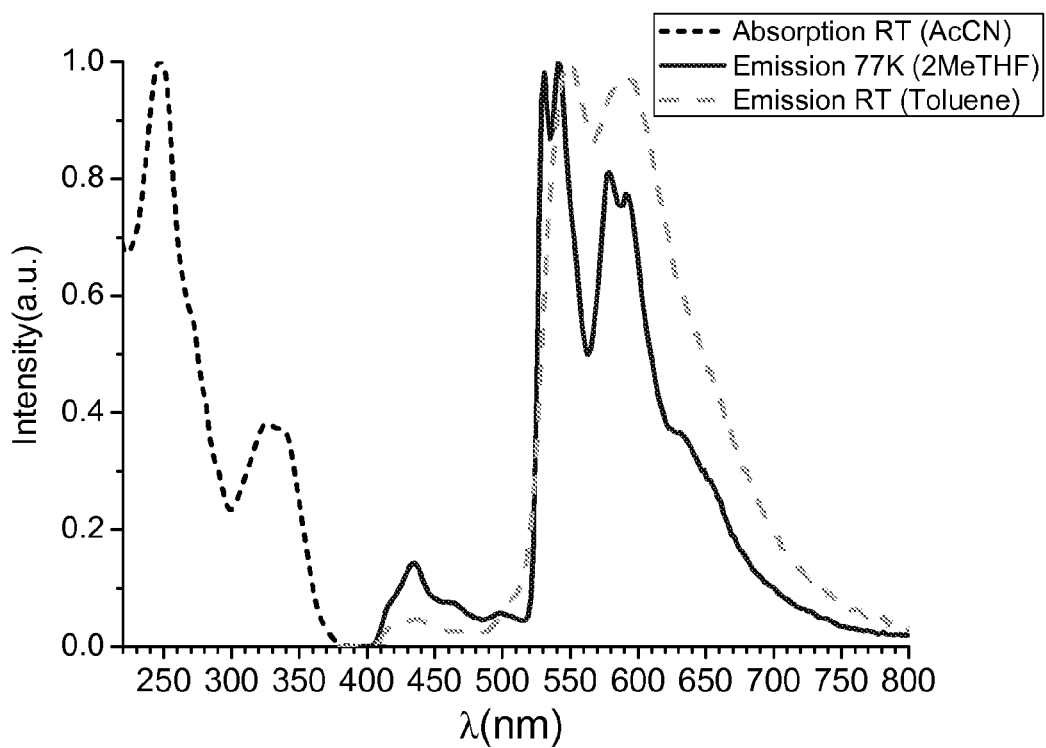
FIG. 18 shows the absorption (acetonitrile) and emission (2MeTHF, 77K; toluene, room temp.) spectra of $Ir(ppz)_2$(CNtBu)(CCPheneatr).
Figure 19:
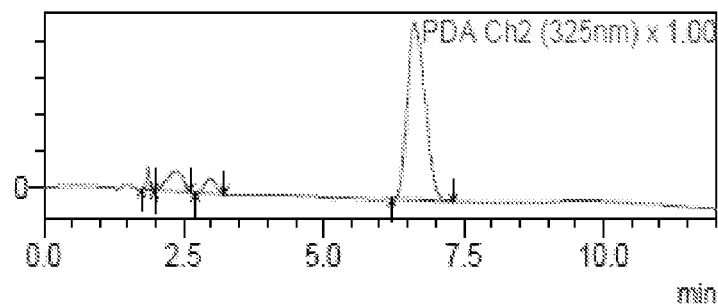
FIG. 19 shows the LCMS (C8, acetonitrile:$H_2O$, 80:20; ESI+) for $Ir(ppz)_2$(CNtBu)(CCPheneatr).
Figure 19:
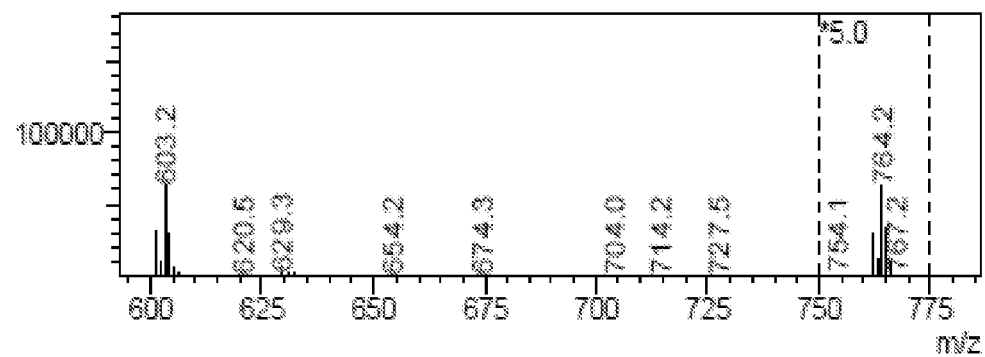
Figure 20:
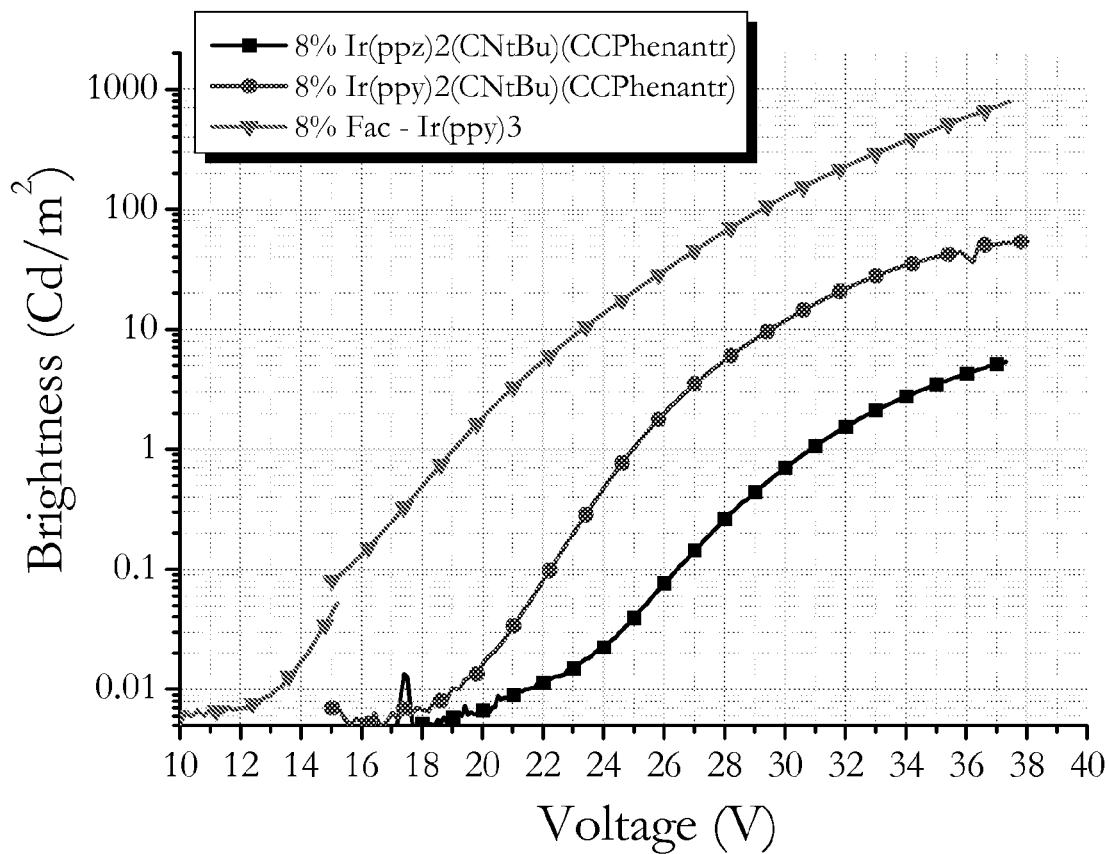
FIG. 20 shows the brightness vs. voltage for devices having the structure ITO/PVK/CBP(Ir complex 8% w/w)/BCP(400 Å)/LiF(10 Å)/Al in which the Ir complex is $Ir(ppy)_2$(CNtBu)(CCPheneatr), $Ir(ppz)_2$(CNtBu)(CCPheneatr) or $Ir(ppy)_3$.
Figure 21:
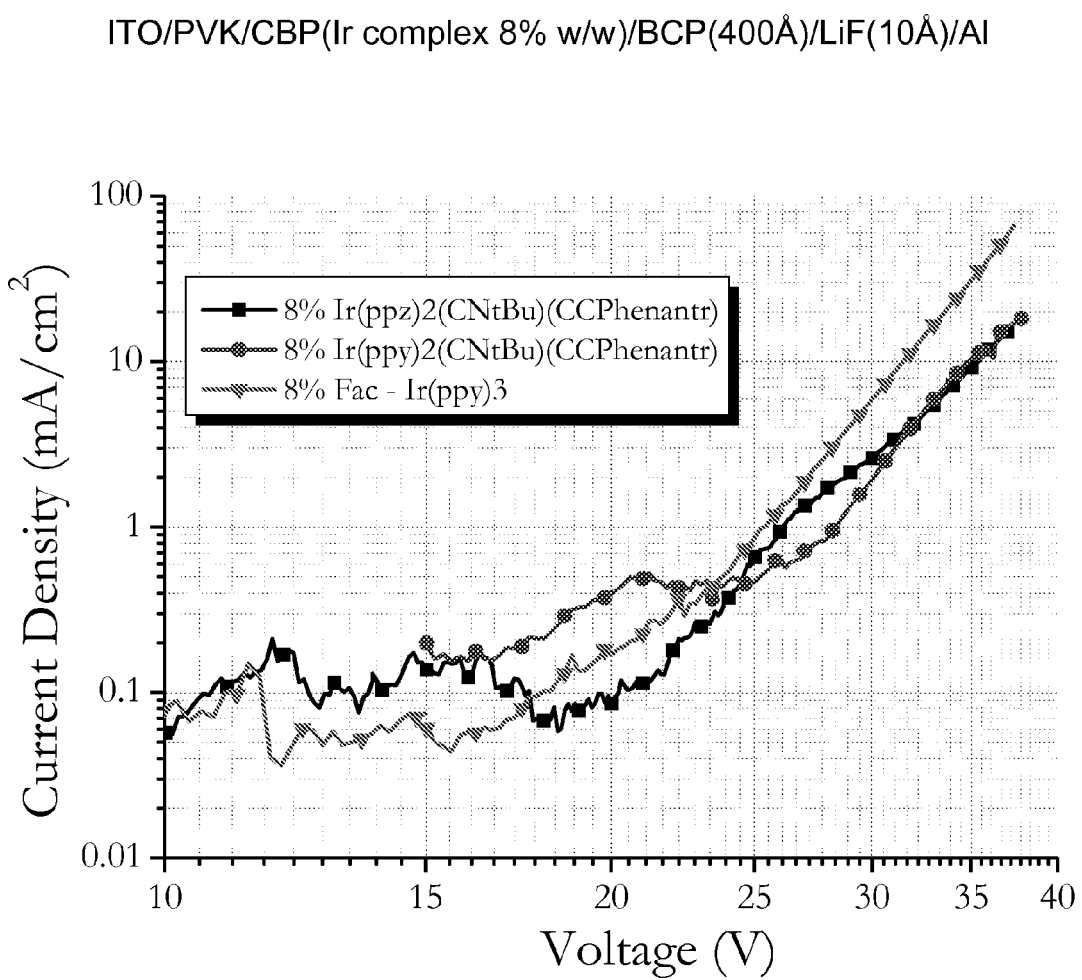
FIG. 21 shows current density vs. voltage for devices having the structure ITO/PVK/CBP(Ir complex 8% w/w)/BCP (400 Å)/LiF(10 Å)/Al in which the Ir complex is $Ir(ppy)_2$(CNtBu)(CCPheneatr), $Ir(ppz)_2$(CNtBu)(CCPheneatr) or $Ir(ppy)_3$.
Figure 22:
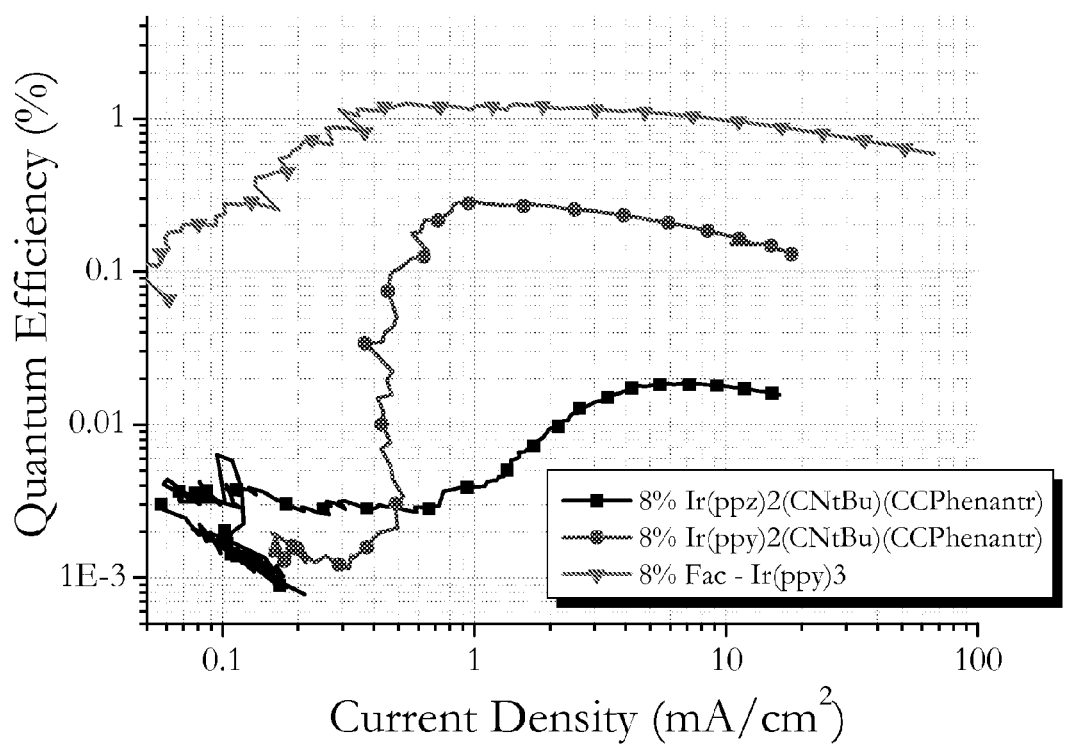
FIG. 22 shows the quantum efficiency vs. current density for devices having the structure ITO/PVK/CBP(Ir complex 8% w/w)/BCP(400 Å)/LiF(10 Å)/Al in which the Ir complex is $Ir(ppy)_2$(CNtBu)(CCPheneatr), $Ir(ppz)_2$(CNtBu)(CCPheneatr) or $Ir(ppy)_3$.
Figure 23:
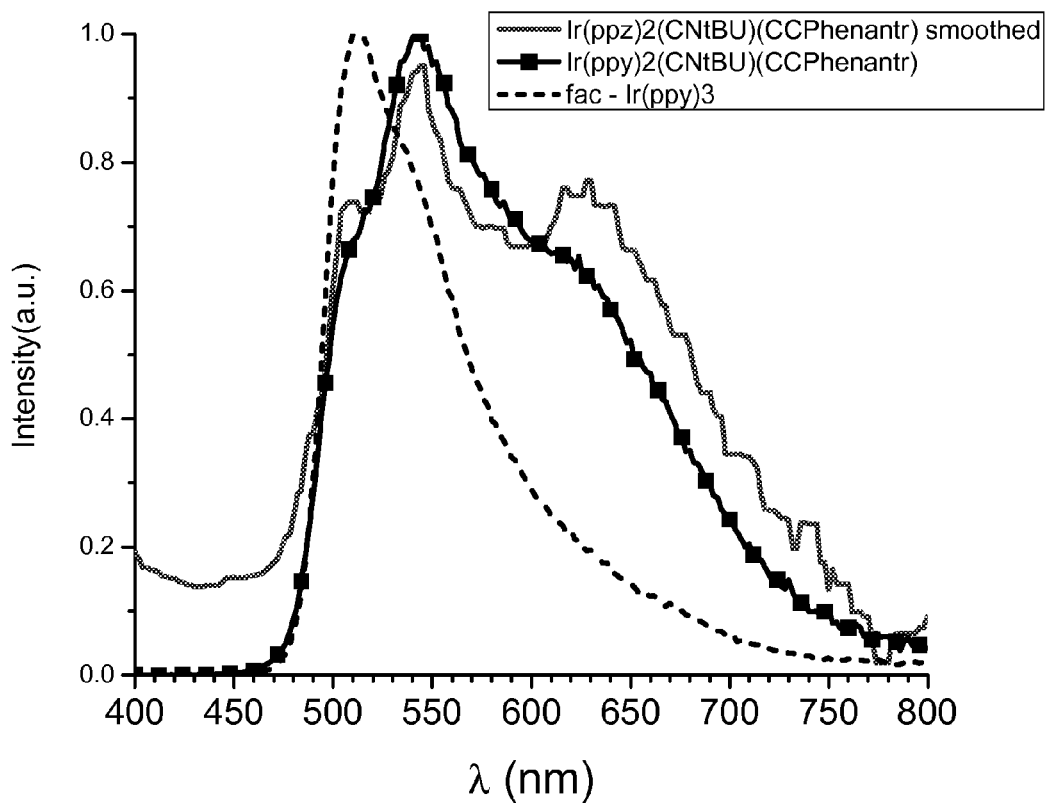
FIG. 23 shows the electroluminescent emission at 30V for devices having the structure ITO/PVK/CBP(Ir complex 8% w/w)/BCP(400 Å)/LiF(10 Å)/Al in which the Ir complex is Ir(ppy)$_2$(CNtBu)(CCPheneatr), Ir(ppz)$_2$(CNtBu)(CCPheneatr) or Ir(ppy)$_3$.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, aralkyl, heterocyclic group, aryl, aromatic group, and heteroaryl are known to the art, and are defined in U.S. Pat. No. 7,279,704 at cols. 31-32, which are incorporated herein by reference.

The devices of the invention have an emissive layer comprising a phosphorescent (triplet-emitting) organometallic material. At least one of the phosphorescent materials in the emissive layer is an Ir(III)cyclometallated alkynyl system. The Ir(III)cyclometallated alkynyl complexes comprise at least one cyclometallating ligand. The cyclometallating ligand is preferably aromatic, with the bonds between the iridium directly to one or more aromatic rings of which the cyclometallating ligand is comprised. The cyclometallating ligand also is preferably bidentate. In preferred embodiments, at least one of the bonds to the cyclometallating ligand is a carbon-iridium bond. The second bond to the cyclometallating ligand may be through a second carbon-iridium bond or through a bond between a heteroatom and the iridium. In particularly preferred embodiments the heteroatom is nitrogen. Thus, in some preferred embodiments, the iridium is bonded to the cyclometallating ligand through a carbon-iridium bond and a nitrogen-iridium bond. The substructure may be represented as:

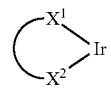

In the above figure, $X^1{\char`\^}X^2$ is a substituted or unsubstituted bidentate cyclometallating ligand. It is preferred that $X^1$, $X^2$, or most preferably both, are a member of an aromatic ring. In preferred embodiments, $X^1$ and $X^2$ are independently selected from C and N.

The bidentate cyclometallating ligand may have the following structure:

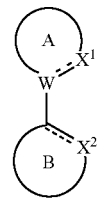

Rings A and B are independently aromatic rings or a fused aromatic rings that bond to the iridium through $X^1$ and $X^2$. $X^1$ and $X^2$ are independently selected from C and N. W is selected from nitrogen and carbon. The dotted lines represent optional double bonds. The rings can be optionally substituted. Optional substituents on the rings include alkyl, alkenyl, alkynyl, aralkyl, CN, $CF_3$, $NR_2$, $NO_2$, OR, halo, and aryl, wherein R is H, alkyl or aryl.

In certain embodiments in which the cyclometallating ligand is a bidentate ligand that is bound to the iridium through a carbon-metal bond and a nitrogen-metal bond to form a cyclometallated ring, cyclometallating ligand may have the following structure:

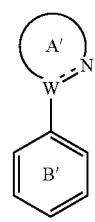

Ring A' is an aromatic heterocyclic ring or a fused aromatic heterocyclic ring with at least one nitrogen atom that coordinates to iridium. W is selected from carbon or nitrogen. Ring B' is a phenyl group that is bonded to the iridium through a carbon atom, and which may additionally be a member of a fused aromatic ring system. The rings can be optionally substituted. Optional substituents on the rings include alkyl, alkenyl, alkynyl, aralkyl, CN, $CF_3$, $NR_2$, $NO_2$, OR, halo, and aryl, wherein R is H, alkyl or aryl.

Representative cyclometallating ligands include:

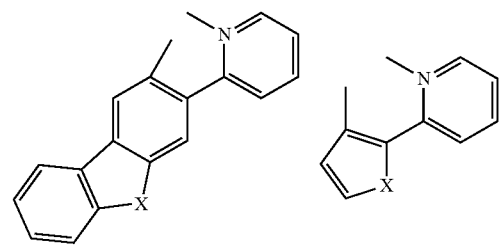

-continued

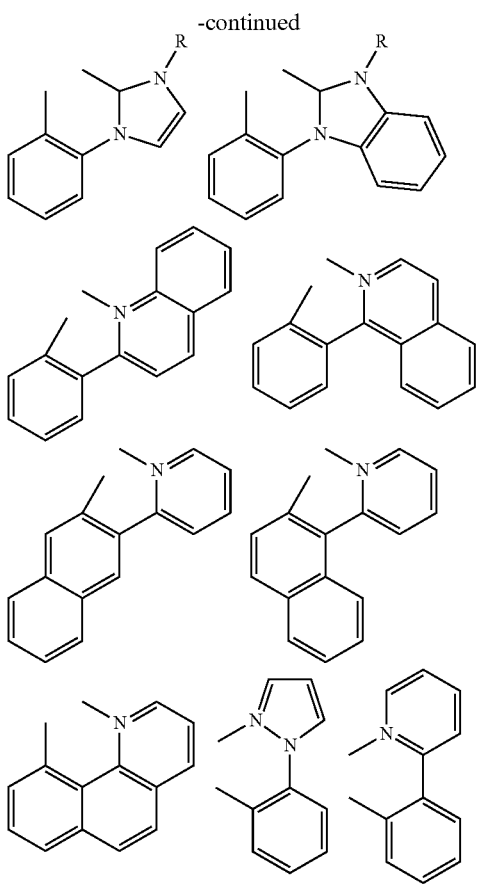

The above cyclometallating ligands may be optionally substituted. Optional substituents on the rings include of alkyl, alkenyl, alkynyl, aralkyl, CN, $CF_3$, $NR_2$, $NO_2$, OR, halo, and aryl. X is NR, $SiR_2$, S and O. R is H, alkyl or aryl.

The Ir(III)cyclometallated alkynyl complexes also comprise at least one bond to an acetylide ligand. The acetylide ligand is bonded to the iridium in the Ir(III)cyclometallated alkynyl complex through an acetylide carbon to provide the substructure Ir—C≡C—$R^1$.

The Ir(III)cyclometallated alkynyl complexes may also comprise an ancillary ligand to fill the coordination sphere of the iridium center. These ligands are referred to as "ancillary" because it is believed that they may modify the photoactive properties of the molecule, as opposed to directly contributing to the photoactive properties. The definitions of photoactive and ancillary are intended as non-limiting theories. The ancillary ligands may be selected from those disclosed in the following references:

U.S. Pat. Application Publ. No. 2002-0034656 (K&K 10020/15303), FIGS. 11-50, U.S. Pat. Application Publ. No. 2003-0072964 (Thompson et al.), paragraphs 7-132; and FIGS. 1-8; U.S. Pat. Application Publ. No. 2002-0182441 (Lamansky et al.), paragraphs 13-165, including FIGS. 1-9(g); U.S. Pat. No. 6,420,057 B1 (Ueda et al.), col. 1, line 57, through col. 88, line 17, including each compound I-1 through XXIV-12; U.S. Pat. No. 6,383,666 B1 (Kim et al.), col. 2, line 9, through col. 21, lin3 67; U.S. Pat. Application Publ. No. 2001-0015432 A1 (Igarashi et al.), paragraphs 2-57, including compounds (1-1) through (1-30); U.S. Pat. Application Publ. No. 2001-0019782 A1 (Igarashi et al.), paragraphs 13-126, including compounds (1-1) through (1-70), and (2-1) through (2-20); U.S. Pat. Application Publ. No. 2002-0024293 (Igarashi et al.), paragraphs 7-95, including general formulas K-I through K-VI, and example compounds (K-1) through (K-25); U.S. Pat. Application Publ. No. 2002-0048689 A1 (Igarashi et al.), paragraphs 5-134, including compounds 1-81, and example compounds (1-1) through (1-81); U.S. Pat. Application Publ. No. 2002-0063516 (Tsuboyama et al.), paragraphs 31-161, including each compound 1-16; U.S. Pat. Application Publ. No. 2003-0068536 (Tsuboyama et al.), paragraphs 31-168, including each compound in Tables 1-17, corresponds to EP-1-239-526-A2; U.S. Pat. Application Publ. No. 2003-0091862 (Tokito et al.), paragraphs 10-190, including each compound in Tables 1-17, corresponds to EP-1-239-526-A2; U.S. Pat. Application Publ. No. 2003-0096138 (Lecloux et al.), paragraphs 8-124, including FIGS. 1-5; U.S. Pat. Application Publ. No. 2002-0190250 (Grushin et al.), paragraphs 9-191; U.S. Pat. Application Publ. No. 2002-0121638 (Grushin et al.), paragraphs 8-125; U.S. Pat. Application Publ. No. 2003-0068526 (Kamatani et al.), paragraphs 33-572, including each compound in Tables 1-23; U.S. Pat. Application Publ. No. 2003-0141809 (Furugori et al.), paragraphs 29-207; U.S. Pat. Application Publ. No. 2003-0162299 A1 (Hsieh et al.), paragraphs 8-42; WO 03/084972, (Stossel et al.), Examples 1-33; WO 02/02714 A2 ((Petrov et al.), pages 2-30, including each compound in Tables 1-5; EP 1-191-613 A1 (Takiguchi et al.), paragraphs 26-87, including each compound in Tables 1-8, (corresponding to U.S. Pat. Application Publ. No. 2002-0064681); and EP 1-191-614 A2 (Tsuboyama et al.), paragraphs 25-86, including each compound in Tables 1-7; which are incorporated herein by reference in their entirety.

In certain embodiments, the ancillary ligand is selected to have the formula —C≡N—$R^3$; wherein $R^3$ is selected from the group consisting of alkyl, cycloalkyl, alkenyl, aryl, aralkyl, and heteroaryl.

In preferred aspects of the invention, the triplet-emitting material is a compound having the formula I:

wherein:
$X^1 \char`\^ X^2$ is a substituted or unsubstituted bidentate cyclometallated aromatic ligand;
$X^1$ and $X^2$ are independently selected from C and N;
Z is an acetylide ligand having the structure:

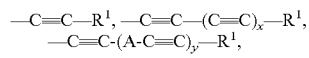

each $R^1$ is independently selected from the group consisting of H, alkyl, cycloalkyl, alkenyl, cycloalkenyl, aryl, heteroaryl, $Si(R^2)_3$, $M(L)_z$, and a heterocyclic group, each of which may be substituted or unsubstituted;
each x is independently selected from 0-5;
each y is independently selected from 0-5;
each $R^2$ is independently selected from H, alkyl, cycloalkyl, alkenyl, cycloalkenyl, aryl, heteroaryl, and a heterocyclic group;
M is a metal atom;
L is a mono-, bi- or tridentate ligand;
z is 0-5;
A is aryl or heteroaryl;
Y is a monodentate ancillary ligand;

a is 1, 2, 3, or 4;
b is 0, 1, 2, or 3;
n is 1 or 2;
the sum of a+b+n is 4 or 5; and
Cat is an optional cation the charge of which provides a net neutral charge for formula I.

In certain preferred embodiments, n is 2, a is 1 and b is 1. In other preferred embodiments, n is 2, a is 2, and b is 0.

In other aspects of the invention, the triplet-emitting material is a compound having the formula II:

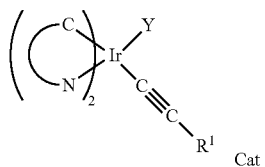

(II)

wherein
C^N is a substituted or unsubstituted cyclometallated ligand;
each $R^1$ is independently selected from the group consisting of H, alkyl, cycloalkyl, alkenyl, cycloalkenyl, aryl, heteroaryl, $Si(R^2)_3$, $M(L)_z$, and a heterocyclic group, each of which may be substituted or unsubstituted;
each $R^2$ is independently selected from H, alkyl, cycloalkyl, alkenyl, cycloalkenyl, aryl, heteroaryl, and a heterocyclic group;
M is a metal atom;
L is a mono-, bi- or tridentate ligand;
z is 0-5;
Y is a monodentate ancillary ligand; and
Cat is an optional cation the charge of which provides a net neutral charge for formula II.

In other aspects of the invention, the triplet-emitting material is a compound having the formula III:

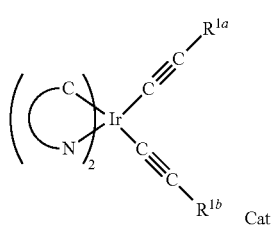

(III)

wherein
C^N is a substituted or unsubstituted cyclometallated ligand;
$R^{1a}$ and $R^{1b}$ are independently selected from the group consisting of
H, alkyl, cycloalkyl, alkenyl, cycloalkenyl, aryl, heteroaryl, $Si(R^2)_3$, $M(L)_z$, and a heterocyclic group, each of which may be substituted or unsubstituted;
each $R^2$ is independently selected from H, alkyl, cycloalkyl, alkenyl, cycloalkenyl, aryl, heteroaryl, and a heterocyclic group;
M is a metal atom;
L is a mono-, bi- or tridentate ligand;
z is 0-5;
and
Cat is an optional cation the charge of which provides a net neutral charge for formula III. In each embodiment that may comprise the cation Cat, the cation may me selected from any appropriate species having a positive charge, including metal cations (such as alkali metal cations) and quaternary ammonium cations.

The acetylide ligand (Z) may accommodate a wide variety of substituent groups (designated $R^1$, $R^{1a}$ or $R^{1b}$ in the above structure). In preferred embodiments, each $R^1$, $R^{1a}$ or $R^{1b}$ is independently selected from:

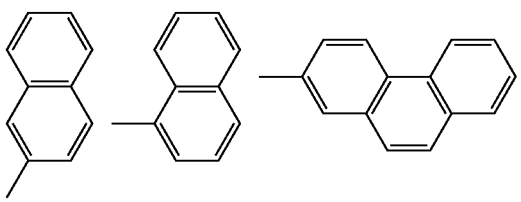

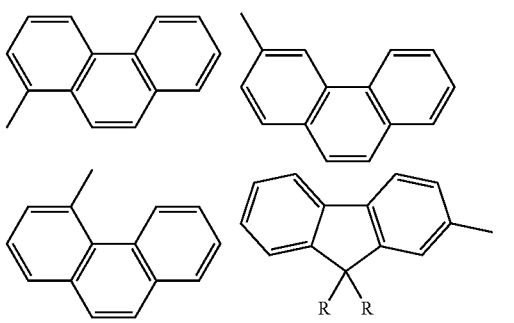

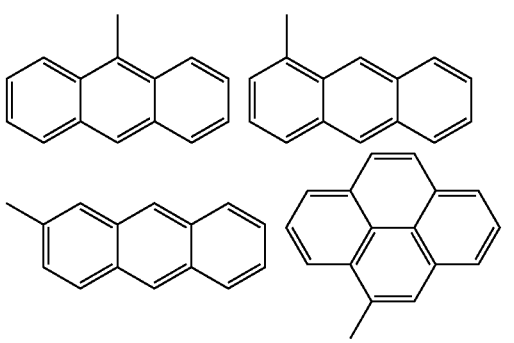

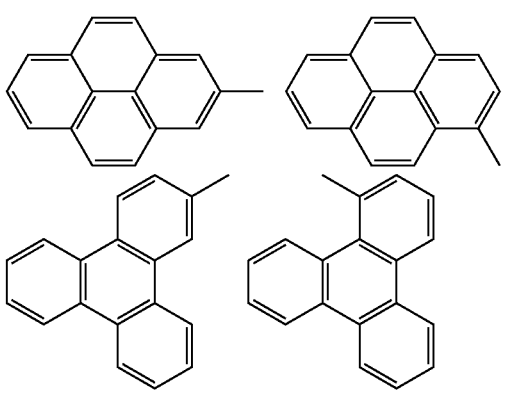

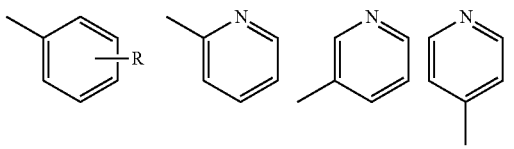

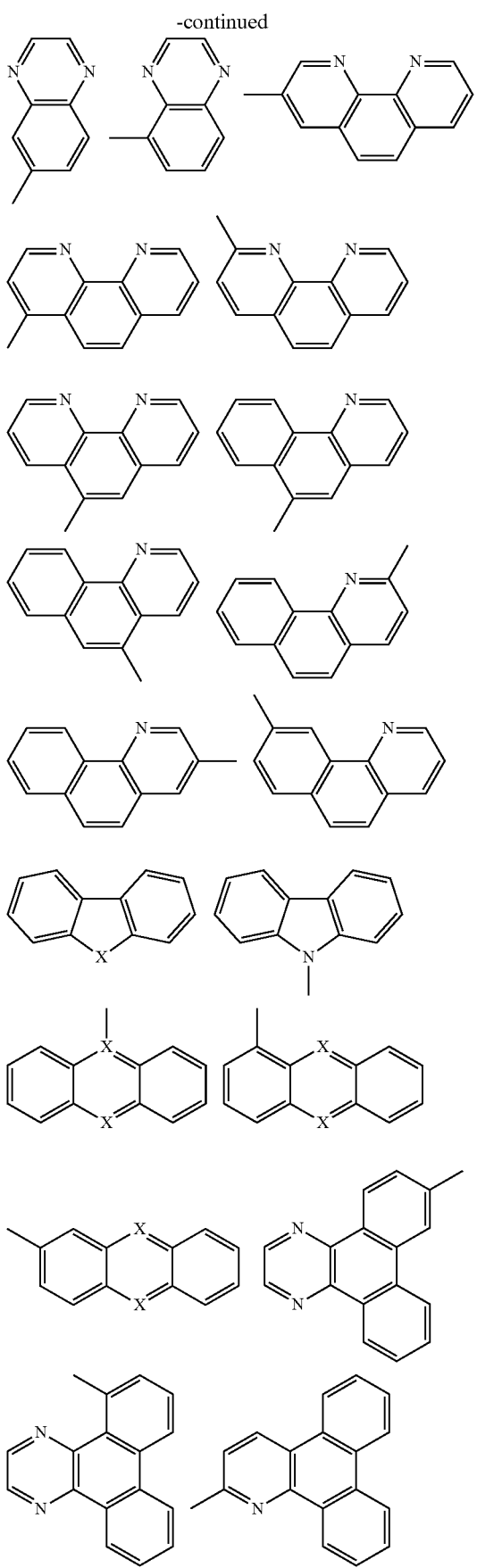
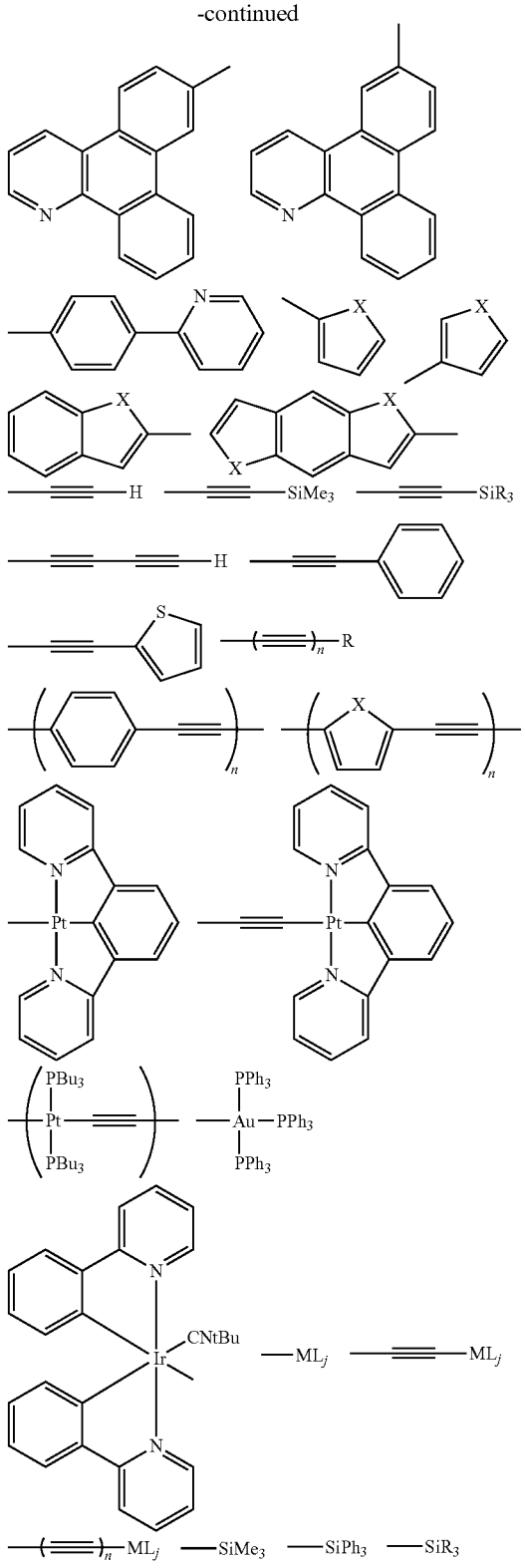
wherein each X is independently selected from C(R')$_d$, N(R')$_e$, S, O, SO, SO$_2$ and Si(R')$_d$;
d is 1 or 2;
e is 0 or 1;
n is 1 to 5;

each R is independently selected from H, halo, CN, alkyl, cycloalkyl, alkenyl, aryl, aralkyl, heteroaryl; OR', NR'$_2$, CO$_2$R', COR', CONR'$_2$, and Si(R')$_3$;
each R' is independently selected from H, alkyl, cycloalkyl, alkenyl, aryl, aralkyl, and heteroaryl;
M is a metal atom; L is a mono-, bi- or tridentate ligand; and j is 0 to 5.

Also, each of the above groups depicted as preferred embodiments of R$^1$, R$^{1a}$ or R$^{1b}$ may be further optionally substituted at any available carbon atom by a substituent selected from halo, CN, alkyl, cycloalkyl, alkenyl, aryl, aralkyl, heteroaryl; OR', NR'$_2$, CO$_2$R', COR', CONR'$_2$, and Si(R')$_3$.

In certain embodiments of the invention, the relative triplet energy of the acetylide ligands and the cyclometallated ligands, allow the tuning of the emission of the claimed complexes, such as that if the triplet energy of the acetylides is lower than the cyclometallating ligands, the emission may be driven by the former group.

An organic light emitting device is also provided. The device may include an anode, a cathode, and an organic emissive layer disposed between the anode and the cathode. The organic emissive layer may include a host and a phosphorescent dopant.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | 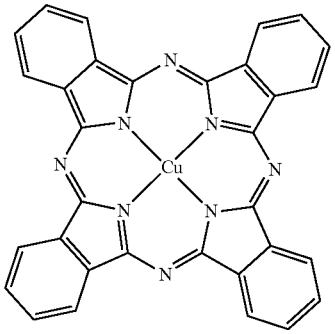 | Appl. Phys. Lett. 69, 2160 (1996) |
| Starburst triarylamines | 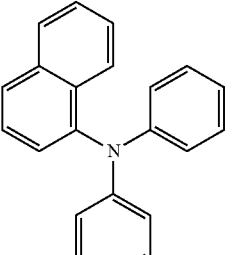 | J. Lumin. 72-74, 985 (1997) |
| CF$_x$ Fluorohydrocarbon polymer |  | Appl. Phys. Lett. 78, 673 (2001) |

TABLE 1-continued
| MATERIAL | EXAMPLES OF MATERIAL | PUBLICATIONS |
|---|---|---|
| Conducting polymers (e.g., PEDOT:PSS, polyaniline, polypthiophene) | 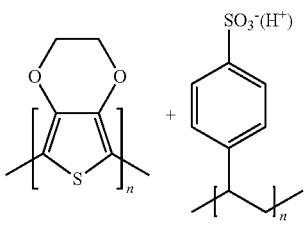 | Synth. Met. 87, 171 (1997) WO2007002683 |
| Phosphonic acid and sliane SAMs | 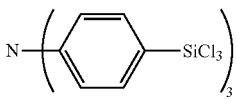 | US20030162053 |
| Triarylamine or polythiophene polymers with conductivity dopants | 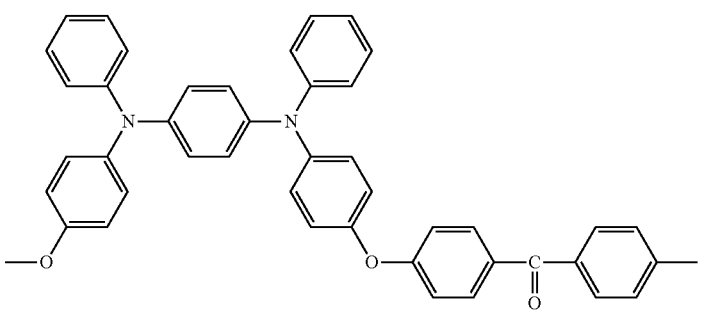 and 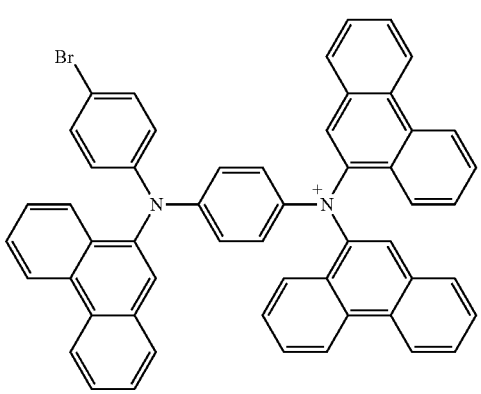 [SMILES: Brc1ccc(N(c2ccc(N(c3cc4ccccc4c4ccccc34)c3cc4ccccc4c4ccccc34)cc2)c2cc3ccccc3c3ccccc23)cc1] 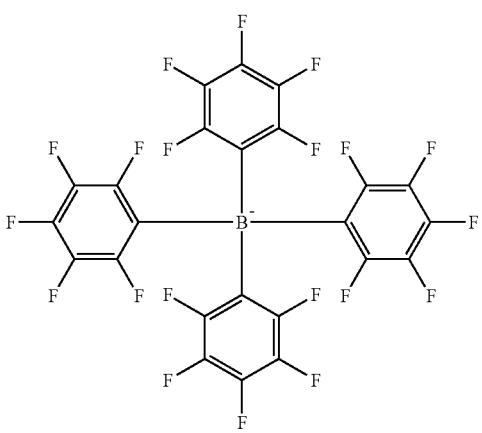 | EA01725079A1 |

TABLE 1-continued
| MATERIAL | EXAMPLES OF MATERIAL | PUBLICATIONS |
|---|---|---|
| Arylamines complexed with metal oxides such as molybdenum and tungsten oxides | 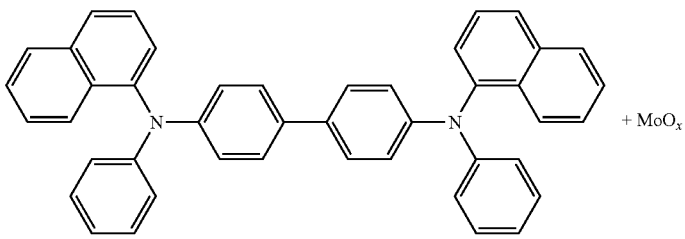 [SMILES: c1ccc(N(c2ccc(-c3ccc(N(c4ccccc4)c4cccc5ccccc45)cc3)cc2)c2cccc3ccccc23)cc1] | SID Symposium Digest, 37, 923 (2006) WO2009018009 |
| p-type semiconducting organic complexes | 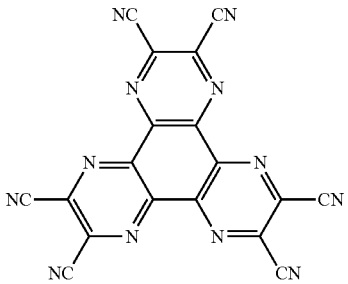 [SMILES: N#Cc1nc2c3nc(C#N)c(C#N)nc3c3nc(C#N)c(C#N)nc3c2nc1C#N] | US20020158242 |
| Metal organometallic complexes | 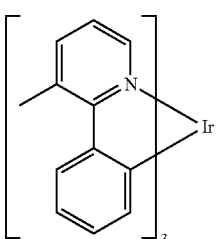 | US20060240279 |
| Cross-linkable compounds | 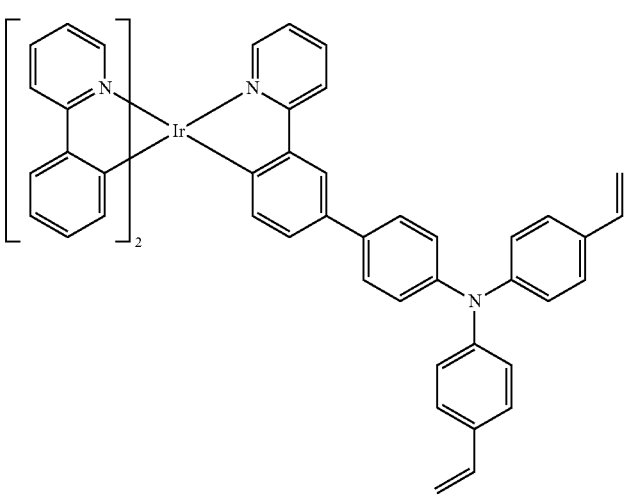 | US20080220265 |
Hole transporting materials
| | | |
|---|---|---|
| Triarylamines (e.g., TPD, α-NPD) | 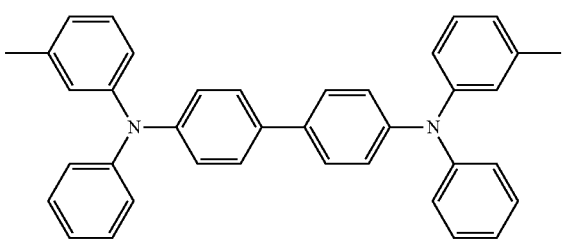 | Appl. Phys. Lett. 51, 913 (1987) |

TABLE 1-continued

| MATERIAL | EXAMPLES OF MATERIAL | PUBLICATIONS |
|---|---|---|
| | | U.S. Pat. No. 5,061,569 |
| | | EP650955 |
| | | J. Mater. Chem. 3, 319 (1993) |

TABLE 1-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |

TABLE 1-continued
| MATERIAL | EXAMPLES OF MATERIAL | PUBLICATIONS |
|---|---|---|
| Triarylamine with (di)benzothiophene/ (di)benzofuran | 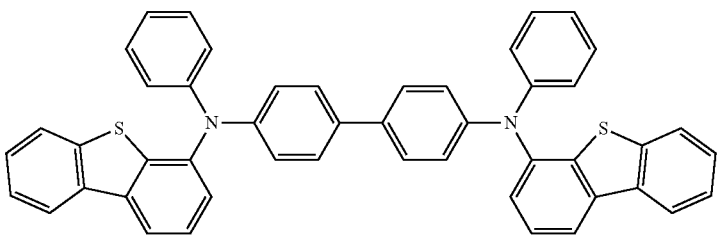 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |
| Indolocarbazoles | 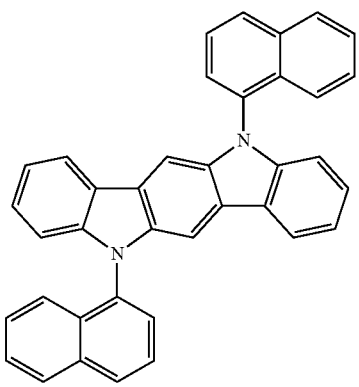 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 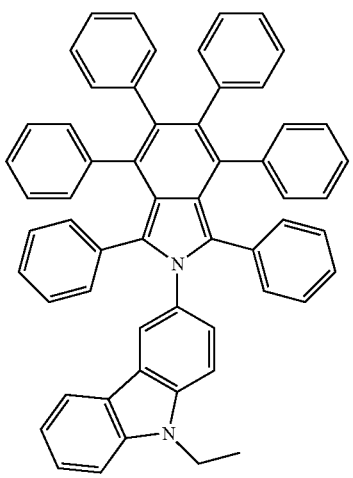 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 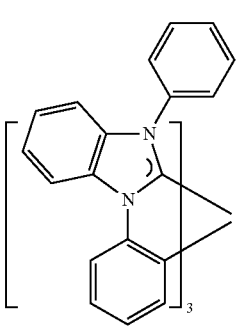 | US20080018221 |

TABLE 1-continued

| MATERIAL | EXAMPLES OF MATERIAL | PUBLICATIONS |
|---|---|---|
| Phosphorescent OLED host materials | | |
| Red hosts | | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 1-continued

| MATERIAL | EXAMPLES OF MATERIAL | PUBLICATIONS |
|---|---|---|
| Aromatic fused rings | | WO2009066779, WO2009066778, WO2009063833, US20090045731, US20090045730, WO2009008311, US20090008605, US20090009065 |
| Zinc complexes | | WO2009062578 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 1-continued
| MATERIAL | EXAMPLES OF MATERIAL | PUBLICATIONS |
|---|---|---|
| | 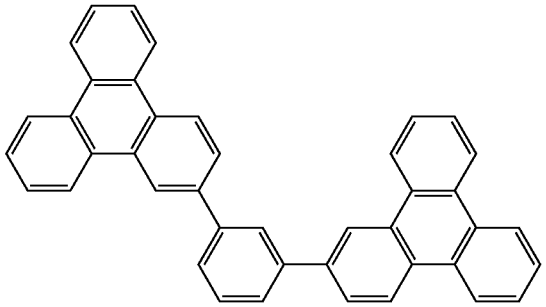 [SMILES: c1cc(-c2ccc3c4ccccc4c4ccccc4c3c2)cc(-c2ccc3c4ccccc4c4ccccc4c3c2)c1] | US20060280965 |
| | 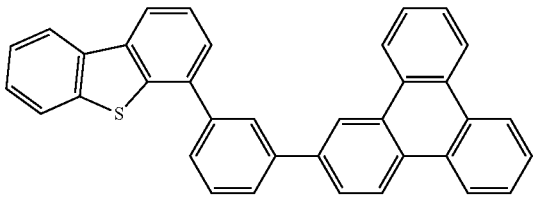 [SMILES: c1cc(-c2ccc3c4ccccc4c4ccccc4c3c2)cc(-c2cccc3c2sc2ccccc23)c1] | WO2009021126 |
| Donor acceptor type molecules | 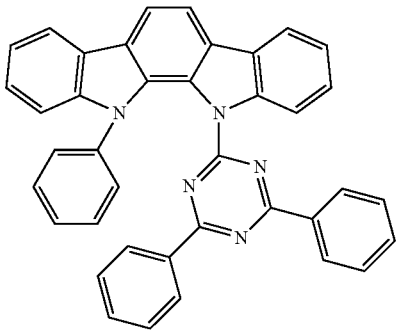 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/DBT/DBF | 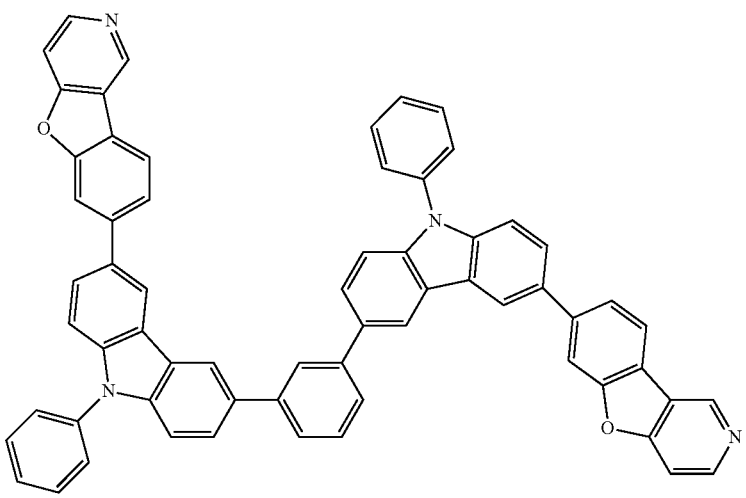 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 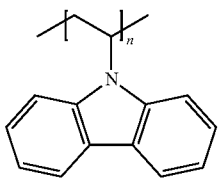 | Appl. Phys. Lett. 77, 2280 (2000) |

TABLE 1-continued
| MATERIAL | EXAMPLES OF MATERIAL | PUBLICATIONS |
|---|---|---|
| Spirofluorene compounds | 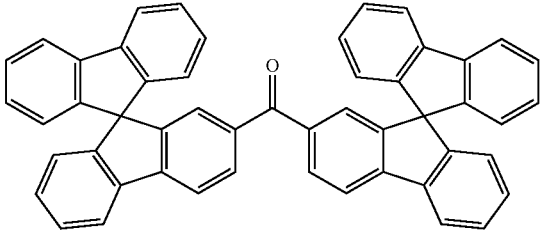 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 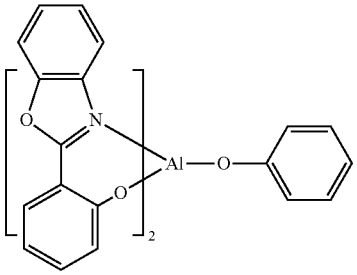 | WO2005089025 |
| | 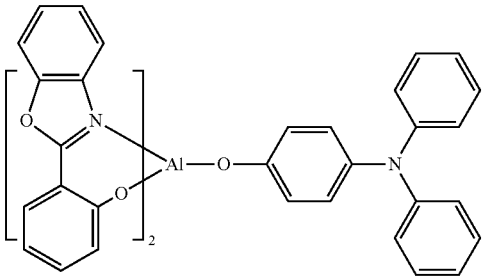 | WO2006132173 |
| | 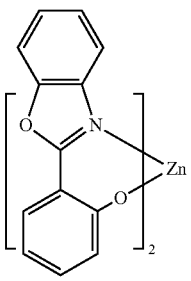 | JP200511610 |
| Spirofluorene-carbazole compounds | 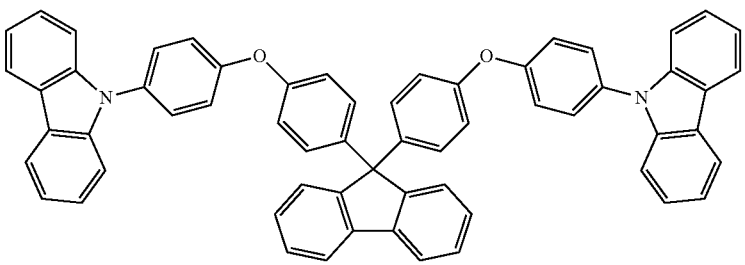 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 1-continued
| MATERIAL | EXAMPLES OF MATERIAL | PUBLICATIONS |
|---|---|---|
| | 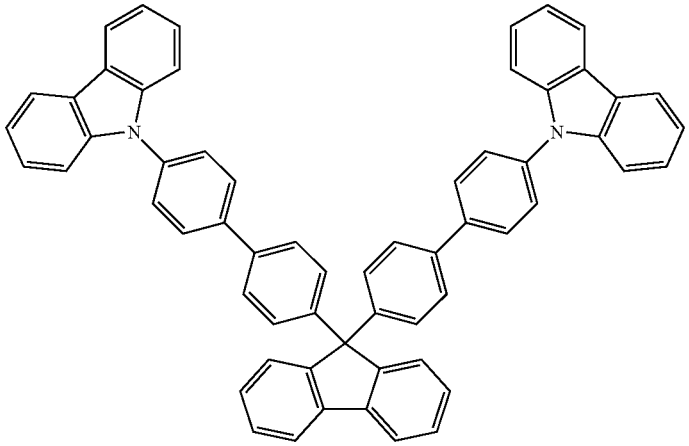 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 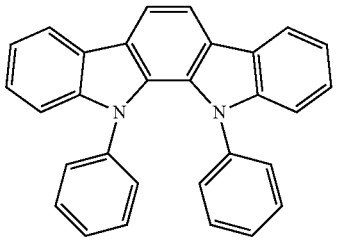 [SMILES: c1ccc(-n2c3ccccc3c3ccc4c5ccccc5n(-c5ccccc5)c4c32)cc1] | WO2007063796 |
| | 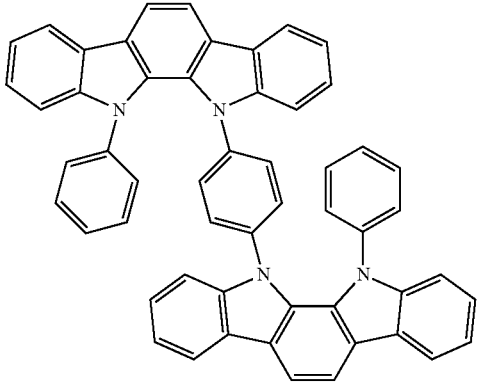 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 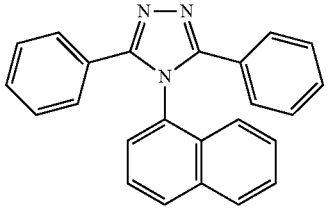 [SMILES: c1ccc(-c2nnc(-c3ccccc3)n2-c2cccc3ccccc23)cc1] | J. Appl. Phys. 90, 5048 (2001) |
| | 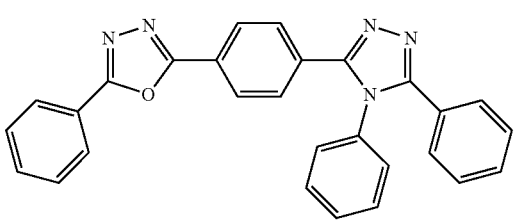 [SMILES: c1ccc(-c2nnc(-c3ccc(-c4nnc(-c5ccccc5)n4-c4ccccc4)cc3)o2)cc1] | WO2004107822 |

TABLE 1-continued
| MATERIAL | EXAMPLES OF MATERIAL | PUBLICATIONS |
|---|---|---|
| Tetraphenylene complexes | 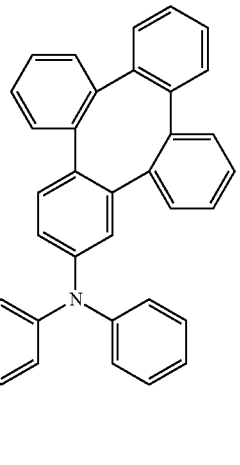 | US20050112407 |
| Metal phenoxypyridine compounds | 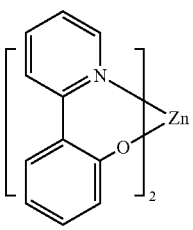 | WO2005030900 |
| Metal coordination complexes (e.g., Zn, Al with N^N ligands) | 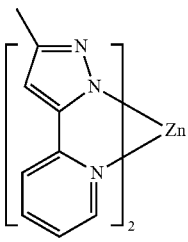 | US20040137268, US20040137267 |
| Blue hosts | | |
| Arylcarbazoles | 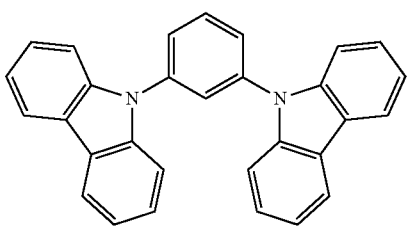 [SMILES: c1cc(-n2c3ccccc3c3ccccc32)cc(-n2c3ccccc3c3ccccc32)c1] | Appl. Phys. Lett, 82, 2422 (2003) |
| | 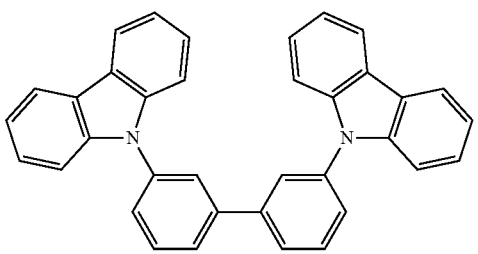 [SMILES: c1cc(-c2cccc(-n3c4ccccc4c4ccccc43)c2)cc(-n2c3ccccc3c3ccccc32)c1] | US20070190359 |

TABLE 1-continued

| MATERIAL | EXAMPLES OF MATERIAL | PUBLICATIONS |
| --- | --- | --- |
| Dibenzothiophene/ Dibenzofuran-carbazole compounds | | WO2006114966, US20090167162 |
| | | US20090167162 |
| | | WO2009086028 |
| | | US20090030202, US20090017330 |
| Silicon aryl compounds | | US20050238919 |
| | | WO2009003898 |

TABLE 1-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| High triplet metal organometallic complex | | U.S. Pat. No. 7,154,114 |

Phosphorescent dopants

Red dopants

| | | |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |

TABLE 1-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 1-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| Platinum(II) organometallic complexes | | WO2003040257 |

TABLE 1-continued
| MATERIAL | EXAMPLES OF MATERIAL | PUBLICATIONS |
|---|---|---|
| Osminum(III) complexes | 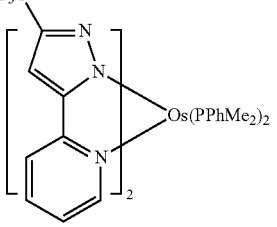 | Chem. Mater. 17, 3532 (2005) |
| Ruthenium(II) complexes | 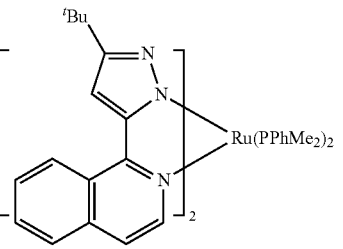 | Adv. Mater. 17, 1059 (2005) |
| Rhenium (I), (II), and (III) complexes | 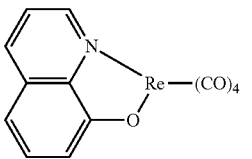 | US20050244673 |
| Green dopants | | |
| Iridium(III) organometallic complexes | 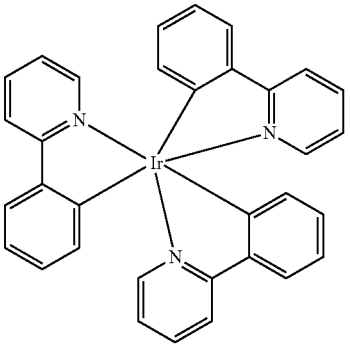  and its derivatives | Inorg. Chem. 40, 1704 (2001) |
| | 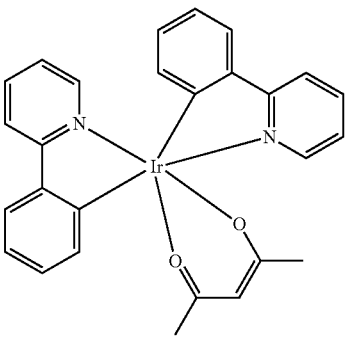 | US20020034656 |

TABLE 1-continued

| MATERIAL | EXAMPLES OF MATERIAL | PUBLICATIONS |
| --- | --- | --- |
| | (structure) | U.S. Pat. No. 7,332,232 |
| | (structure) | US20090108737 |
| | (structure) | US20090039776 |
| | (structure) | U.S. Pat. No. 6,921,915 |

TABLE 1-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US 20060008670<br>JP2007123392 |
| | | Adv. Mater. 16, 2003 (2004) |

TABLE 1-continued
| MATERIAL | EXAMPLES OF MATERIAL | PUBLICATIONS |
|---|---|---|
| | 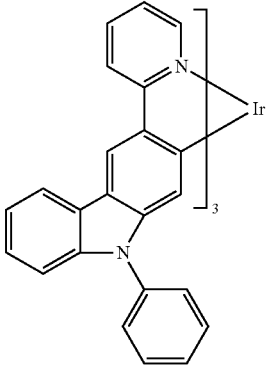 | Angew. Chem. Int. Ed. 2006, 45, 7800 |
| | 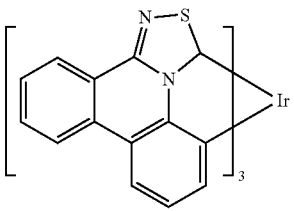 | WO2009050290 |
| | 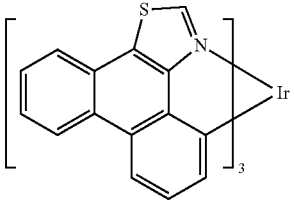 | US20090165846 |
| | 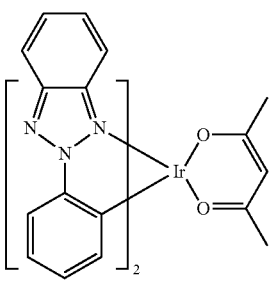 | US20080015355 |
| Monomer for polymeric metal organometallic compounds | 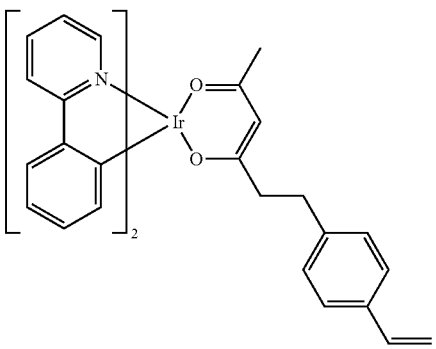 | U.S. Pat. No. 7,250,226, U.S. Pat. No. 7,396,598 |

TABLE 1-continued
| MATERIAL | EXAMPLES OF MATERIAL | PUBLICATIONS |
|---|---|---|
| Pt(II) organometallic complexes, including polydentated ligands | 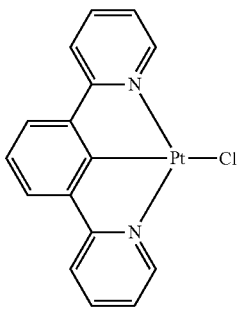 | Appl. Phys. Lett. 86, 153505 (2005) |
| | 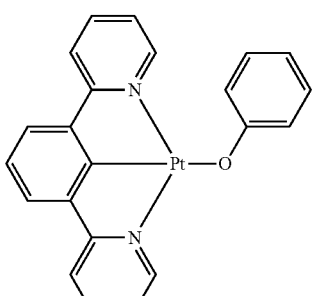 | Appl. Phys. Lett. 86, 153505 (2005) |
| | 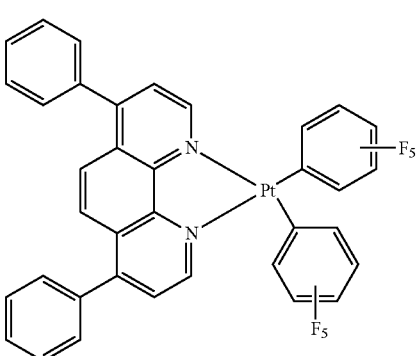 | Chem. Lett. 34, 592 (2005) |
| | 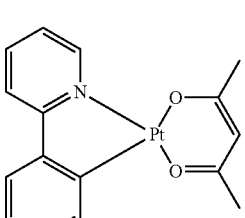 | WO2002015645 |
| | 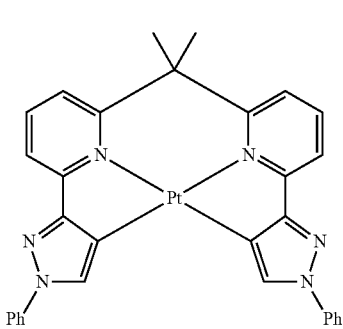 | US20060263635 |

TABLE 1-continued

| MATERIAL | EXAMPLES OF MATERIAL | PUBLICATIONS |
|---|---|---|
| Cu complexes | | WO2009000673 |
| Gold complexes | | Chem. Commun. 2906 (2005) |
| Rhenium(III) complexes | | Inorg. Chem. 42, 1248 (2003) |
| Deuterated organometallic complexes | | US20030138657 |

TABLE 1-continued
| MATERIAL | EXAMPLES OF MATERIAL | PUBLICATIONS |
|---|---|---|
| Organometallic complexes with two or more metal centers | 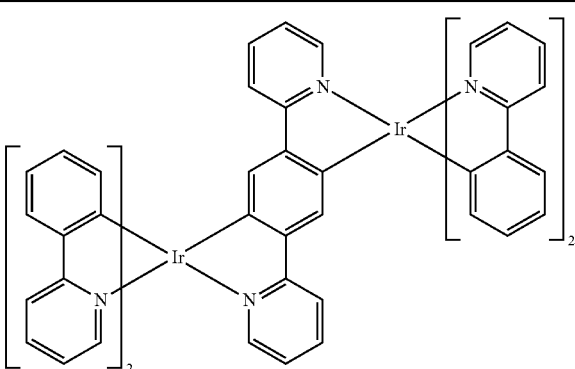 | US20030152802 |
| | 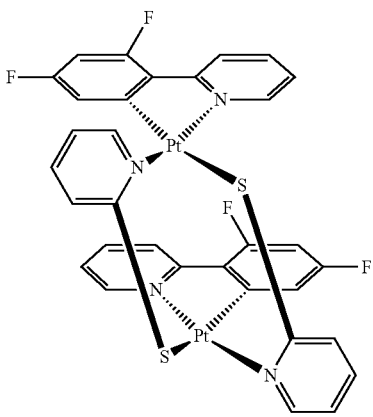 | U.S. Pat. No. 7,090,928 |
| Blue dopants | | |
| Iridium(III) organometallic complexes | 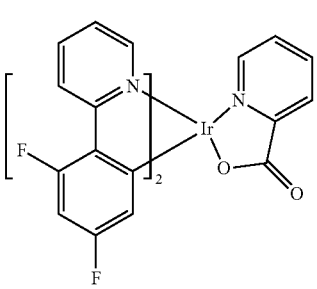 | WO2002002714 |
| | 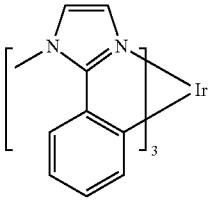 | WO2006009024 |
| | 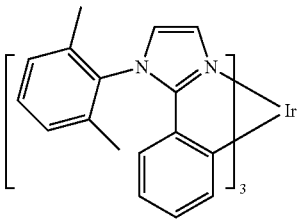 | US20060251923 |

TABLE 1-continued
| MATERIAL | EXAMPLES OF MATERIAL | PUBLICATIONS |
|---|---|---|
| | 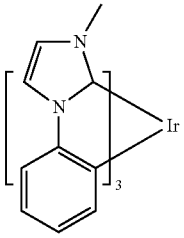 | U.S. Pat. No. 7,393,599, WO2006056418, US20050260441, WO2005019373 |
| | 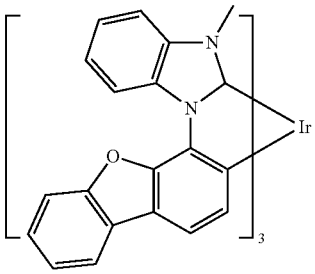 | U.S. Pat. No. 7,534,505 |
| | 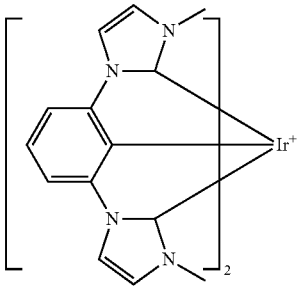 | U.S. Pat. No. 7,445,855 |
| | 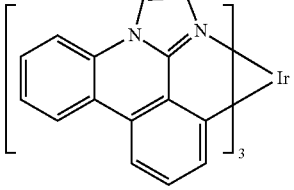 | US20070190359, US20080297033 |
| | 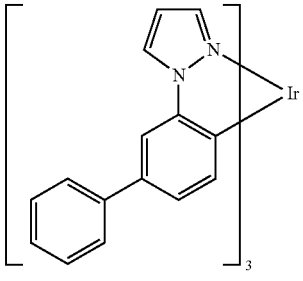 | U.S. Pat. No. 7,338,722 |
| | 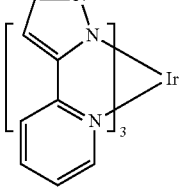 | US20020134984 |

TABLE 1-continued
| MATERIAL | EXAMPLES OF MATERIAL | PUBLICATIONS |
|---|---|---|
| | 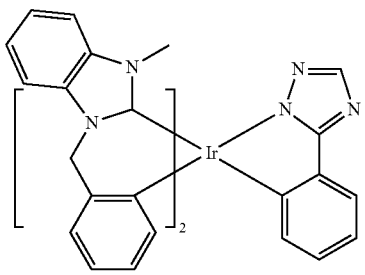 | Angew. Chem. Int. Ed. 47, 1 (2008) |
| | 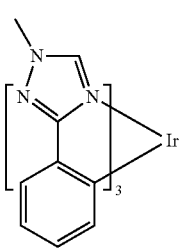 | Chem. Mater. 18, 5119 (2006) |
| | 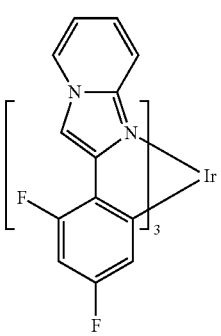 | Inorg. Chem. 46, 4308 (2007) |
| | 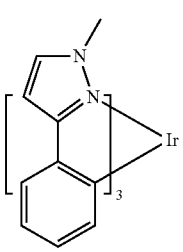 | WO2005123873 |
| | 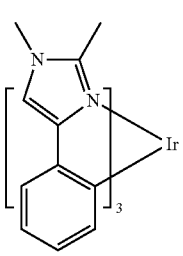 | WO2005123873 |
| | 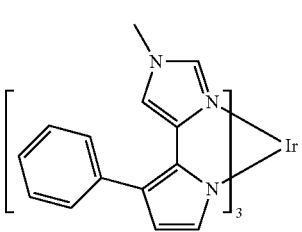 | WO2007004380 |

TABLE 1-continued

| MATERIAL | EXAMPLES OF MATERIAL | PUBLICATIONS |
|---|---|---|
| | | WO2006082742 |
| Osmium(II) complexes | | U.S. Pat. No. 7,279,704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE 1-continued

| MATERIAL | EXAMPLES OF MATERIAL | PUBLICATIONS |
|---|---|---|
| Exciton/hole blocking layer materials | | |
| Bathocuprine compounds (e.g., BCP, BPhen) | 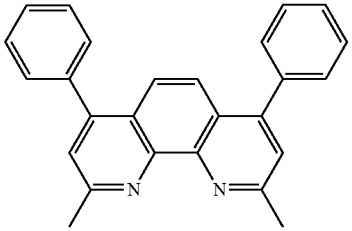 [SMILES: Cc1cc(-c2ccccc2)c2ccc3c(-c4ccccc4)cc(C)nc3c2n1] | Appl. Phys. Lett. 75, 4 (1999) |
| | 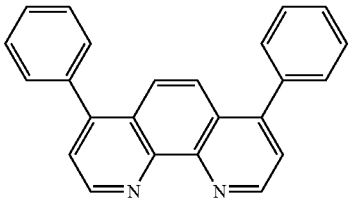 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 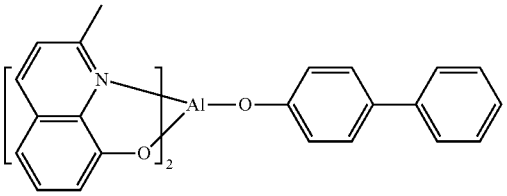 | Appl. Phys. Lett. 81, 162 (2002) |
| 5-member ring electron deficient heterocycles such as triazole, oxadiazole, imidazole, benzoimidazole | 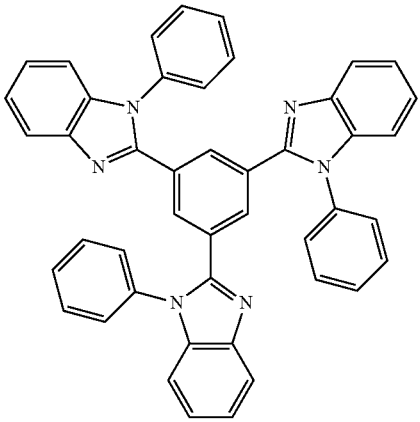 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 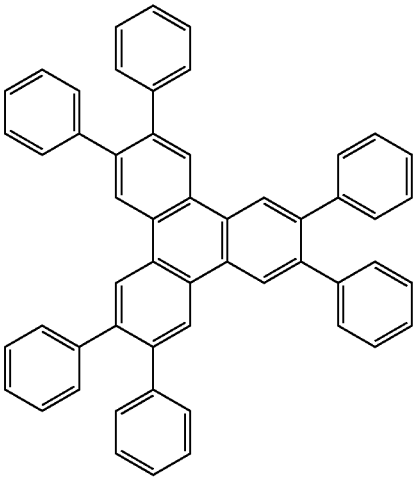 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 1-continued
| MATERIAL | EXAMPLES OF MATERIAL | PUBLICATIONS |
|---|---|---|
| Fluorinated aromatic compounds | 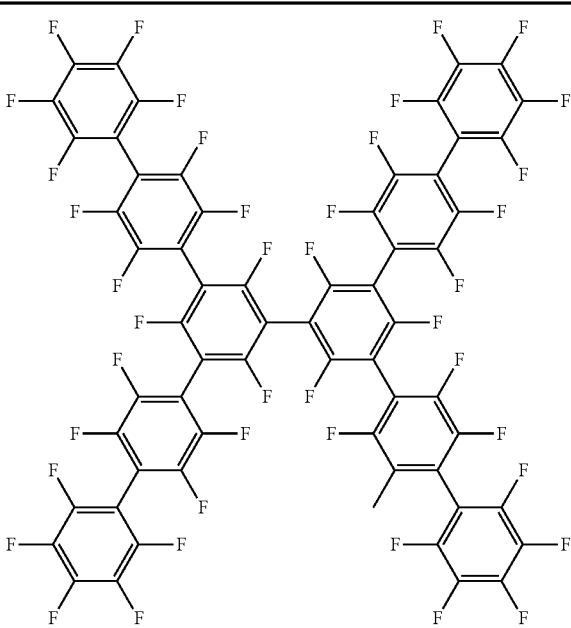 | Appl. Phys. Lett. 79, 156 (2001) |
| Phenothiazine-S-oxide | 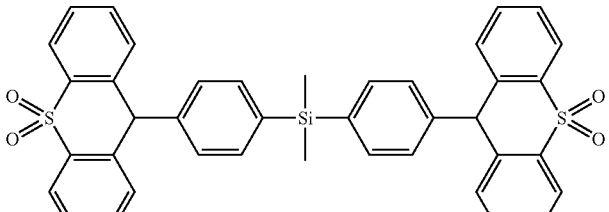 | WO2008132085 |
| Electron transporting materials | | |
| Anthracene-benzoimidazole compounds | 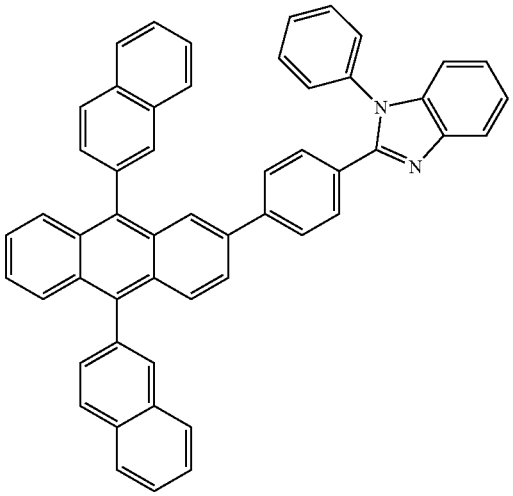 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 1-continued

| MATERIAL | EXAMPLES OF MATERIAL | PUBLICATIONS |
|---|---|---|
|  |  | US20090179554 |
| Aza triphenylene derivatives |  | US20090115316 |
| Anthracene-benzothiazole compounds |  | Appl. Phys. Lett. 89, 063504 (2006) |
| Metal 8-hydroxyquinolates (e.g., $Alq_3$, $Zrq_4$) |  | Appl. Phys. Lett. 51, 913 (1987)<br>U.S. Pat. No. 7,230,107 |
| Metal hydroxybenoquinolates |  | Chem. Lett. 5, 905 (1993) |
| Bathocuprine compounds such as BCP, BPhen, etc |  | Appl. Phys. Lett. 91, 263503 (2007) |

TABLE 1-continued
| MATERIAL | EXAMPLES OF MATERIAL | PUBLICATIONS |
| --- | --- | --- |
| | 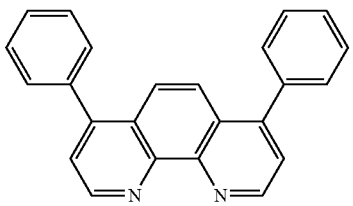 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 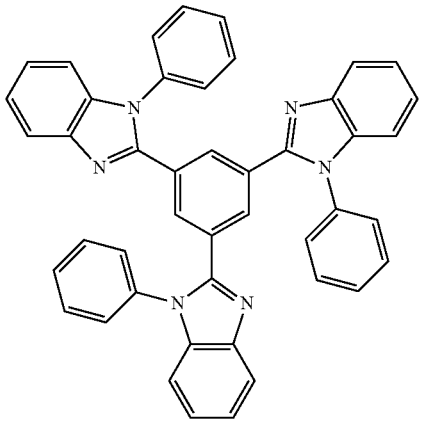 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 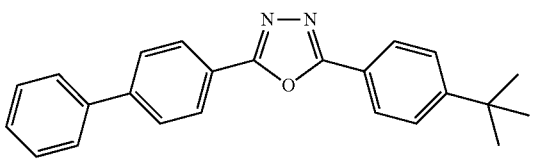 [SMILES: CC(C)(C)c1ccc(-c2nnc(-c3ccc(-c4ccccc4)cc3)o2)cc1] | Appl. Phys. Lett. 55, 1489 (1989) |
| | 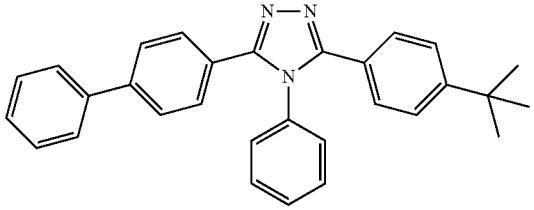 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 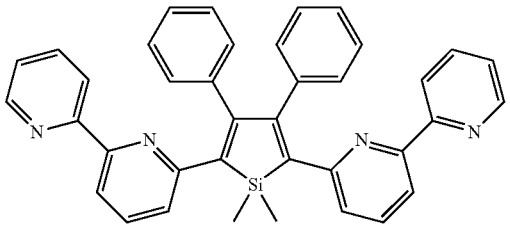 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 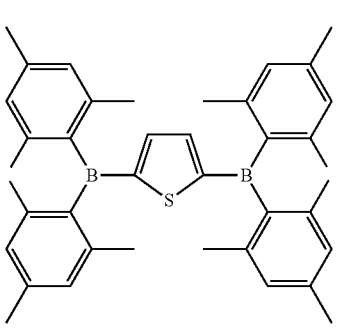 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |

TABLE 1-continued

| MATERIAL | EXAMPLES OF MATERIAL | PUBLICATIONS |
| --- | --- | --- |
| Fluorinated aromatic compounds | | J. Am. Chem. Soc. 122, 1832 (2000) |
| Fullerene (e.g., C60) | | US20090101870 |
| Triazine complexes | | US20040036077 |
| Zn (N^N) complexes | | U.S. Pat. No. 6,528,187 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

EXPERIMENTAL

Iridium Complex Synthesis/Absorption/Emission

The general reactions follow the procedure reported in literature by Fornies et al. *Dalton trans.* 2003, 822-830; W. Weng, et al. *J. Am. Chem. Soc.* 1995, 117, 11922-11931 and modified by disclosed below. The general synthesis was performed as follows:

Example 1 a) Synthesis of the (C∧N)$_2$Ir(CNtBu)Otf (Scheme 1)

1 equivalent of ((C∧N)$_2$Ir μCl)$_2$, synthesized by the Nonoyama's procedure (M. Nonoyama, *Bull. Chem. Soc. Jap.* 1974, 47, 767), is reacted with and 2.05 equivalents of tert-butylisocyanide in CH$_2$Cl$_2$ at room temperature for 1 hour. The mixture is flash chromatographed through Silica with CH$_2$Cl$_2$ to remove less polar impurities; the product is collected using CH$_2$Cl$_2$/MeOH 95/5; removing the solvent and washing the residue with MeOH to afford the clean (C∧N)$_2$Ir(CNtBu)Cl.

(C∧N)₂Ir(CNtBu)Cl is converted in the corresponding trifluoromethanesulfonate (OTf) by reacting its solution in CH₂Cl₂ with 1.1 equivalent of AgOTf dissolved in MeOH at room temperature for 1 h. (J. Li et al., *Polyhedron,* 2004, 23 (2-3), 419-428). The precipitate of AgCl was removed filtering the suspension through celite. The solvent is removed affording the (C∧N)₂Ir(CNtBu)OTf.

Scheme 1: Synthesis of the Ir(III)trifluoremetanesulfonate precursors.

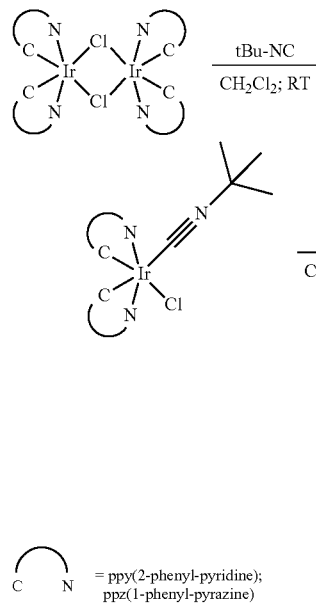

b) Synthesis of the (C∧N)₂Ir(CNtBu)(CCAr)

To a solution of (C∧N)₂Ir(CNtBu)OTf in dry THF at −78° C., a solution of fresh LiC≡CAr (2-4 equivalents) prepared from HC≡CAr (1.1 equivalents) and nBuLi (1 equivalent) in dry THF at −78° C. was added drop wise via cannula. The mixture is reacted for 1 h at −78° C. and the temperature allowed to reach RT over 2 hours.

The solvent is removed and the crude crystallized from ethyl acetate/hexane or diethylether/hexane. The clean product is obtained.

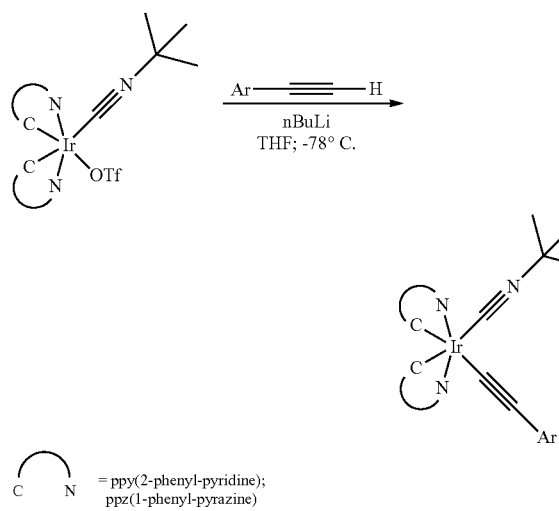

Ar = aliphatic chain, aromatic, heteroaromatic PAH

Example 2 c) Synthesis of the (C∧N)₂Ir(MeOH)₂OTf 1 equivalent of ((C∧N)₂Ir μCl)₂, prepared by the Nonoyama's procedure (M. Nonoyama, *Bull. Chem. Soc. Jap.* 1974, 47, 767) is converted in the corresponding trifluoromethanesulfonate (OTf) by treating its solution in CH₂Cl₂ with 2.2 equivalent of AgOTf dissolved in MeOH at room temperature for 1 h. (J. Li et al. *Polyhedron,* 2004, 23 (2-3), 419-428). The precipitate of AgCl was removed by filtering the suspension through celite. The solvent is removed affording the (C∧N)₂Ir(MeOH)₂OTf

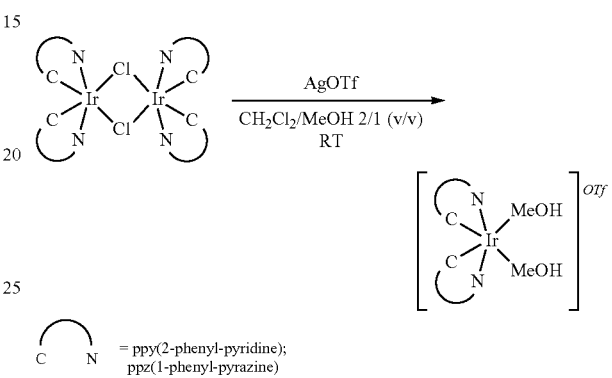

d) Synthesis of the [(C∧N)₂Ir(CCAr)₂]Li

To a solution of (C∧N)₂Ir(MeOH)₂OTf in dry THF at −78° C. a solution of fresh LiC≡CAr (4-6 equivalents) prepared from HC≡CAr (1.1 equivalents) and nBuLi (1 equivalent) in dry THF at −78° C. was added drop wise via cannula. The mixture is reacted for 1 h at −78° C. and the temperature allowed to reach RT over 2 hours.

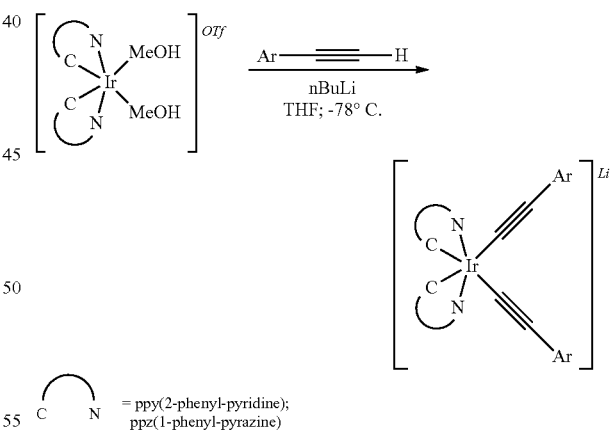

Ar = aliphatic chain, aromatic, heteroaromatic PAH

Example 3

Synthesis of the Ir(ppz)₂(CNtBu)OTf 1.073 g of ((ppz)₂IrμCl)₂ (1.043 mmol) dissolved in 20 mL of CH₂Cl₂ at room temperature was reacted with 0.25 mL of tert-butylisocyanide (2.08 mmol) for 1 hour. The mixture was flash chromatographed through silica with CH₂Cl₂ to remove the less polar impurities and the product was eluted using CH$_2$Cl$_2$/MeOH 95/5. Removing the solvent and washing the residue with MeOH afforded 830 mg of clean Ir(ppz)$_2$(CNtBu)Cl (71% yield).

$^1$H NMR (400 MHz, CDCl$_3$, ppm): 1.40 (9H, s); 6.15 (1H, dd, J=1.6, 7.2 Hz); 6.28 (1H, dd, J=1.2, 7.6 Hz); 6.61 (1H, m); 6.66 (1H, dt, J=1.2, 7.6 Hz); 6.71 (1H, m); 6.74 (1H, dt, J=1.2, 7.2 Hz); 6.85 (2H, m); 7.15 (2H, t, J=7.6 Hz); 7.90 (1H, d, J=2.4 Hz); 8.02 (1H, d, J=2.8 Hz); 8.09 (1H, d, J=2.6 Hz); 8.37 (1H, d, J=2.6 Hz).

500 mg of Ir(ppz)$_2$(CNtBu)Cl (0.84 mmol), dissolved in 50 mL of CH$_2$Cl$_2$, and 236 mg of AgOTf (0.92 mmol) dissolved in 25 mL MeOH were added at room temperature. The mixture was reacted for 2 h. The precipitate of AgCl was removed by filtering the suspension through celite. The solvent was removed affording 626 mg Ir(ppz)$_2$(CNtBu)OTf (>99% yield).

$^1$H NMR (400 MHz, CD$_3$CN, ppm): 1.40 (9H, s); 6.08 (2H, t, J=7.2 Hz); 6.71 (1H, dt, J=1.47, 7.9 Hz); 6.81 (2H, m); 6.87 (1H, t, J=2.64 Hz); 6.95 (1H, dt, J=1.17, 7.63 Hz); 7.00 (1H, dt, J=1.17, 7.63 Hz); 7.38 (1H, dd, J=1.17, 7.63 Hz); 7.41 (1H, dd, J=1.17, 7.92 Hz); 8.06 (1H, d, J=2.1 Hz); 8.11 (1H, d, J=2.3 Hz); 8.41 (1H, d, J=2.93 Hz); 8.43 (1H, d, J=2.93 Hz).

$^{19}$F NMR (376 MHz, CD$_3$CN, ppm): −79.3 (s).

Example 4

Synthesis of the Ir(ppy)$_2$(CNtBu)OTf 482 mg of ((ppy)$_2$Ir μCl)$_2$ (0.45 mmol) suspended in 10 mL of CH$_2$Cl$_2$ at room temperature was reacted with 0.11 mL of tertButylisocyanide (0.92 mmol) for 1 hour. The clear solution was flash chromatographed through Silica with CH$_2$Cl$_2$ to remove less polar impurities and the product was eluted using CH$_2$Cl$_2$/MeOH 95/5. Removing the solvent and washing the residue with MeOH afforded 405 mg of clean Ir(ppy)$_2$(CNtBu)Cl (72% yield).

$^1$H NMR (400 MHz, CDCl3, ppm): 1.323 (9H, s); 6.10 (1H, dd, J=1.6, 6.97 Hz); 6.33 (1H, dd, J=1.6, 7.5 Hz); 6.73 (1H, dt, J=1.6, 7.78 Hz); 6.79 (1H, dt, J=1.3, 7.2 Hz); 6.85 (2H, tt, 1.34, 7.5 Hz); 7.13 (1H, m); 7.24 (1H, m); 7.56 (2H, m); 7.83 (4H, m); 9.08 (1H, d, J=6.35 Hz); 9.91 (1H, d, J=6.35 Hz).

400 mg of Ir(ppy)$_2$(CNtBu)Cl (0.646 mmol) dissolved in 40 mL of CH$_2$Cl$_2$ and 265 mg of AgOTf (1.03 mmol) dissolved in 20 mL MeOH were added at room temperature, and the mixture was reacted for 2 h. The precipitate of AgCl was removed by filtering the suspension through celite. The solution was diluted with 20 mL of ethyl ether and washed with water. The aqueous phase was back extracted with CH$_2$Cl$_2$ and the organic phases combined. The organic solvent was removed under reduced pressure affording 386 mg Ir(ppy)$_2$(CNtBu)OTf (78% yield).

$^1$H NMR (400 MHz, CD$_3$CN, ppm): 1.34 (9H, s); 6.05 (1H, d, J=7.63 Hz); 6.13 (1H, d, J=7.63 Hz); 6.78 (1H, t, J=7.05 Hz); 6.85 (1H, t, J=7.05 Hz); 6.95 (2H, m); 7.43 (2H, m); 7.69 (1H, d, J=7.63 Hz); 7.72 (1H, d, J=7.63 Hz); 8.10 (4H, m); 9.03 (1H, d, J=5.57 Hz); 9.08 (1H, d, J=5.87 Hz).

$^{19}$F NMR (376 MHz, CD$_3$CN, ppm): −79.3 (s).

Example 5

Synthesis of the Ir(ppy)$_2$(MeOH)$_2$ OTf 300 mg of ((ppy)$_2$Ir μCl)$_2$ (0.28 mmol) suspended in 30 mL of CH$_2$Cl$_2$ at room temperature and 158 mg of AgOTf (0.61 mmol) dissolved in 10 mL MeOH were added at room temperature, and the mixture was reacted for 2 h. The precipitate of AgCl was removed by filtering the suspension through celite. The solvent was removed under reduced pressure and the crude product was crystallized from CH$_2$Cl$_2$— hexane affording 420 mg Ir(ppy)$_2$(MeOH)$_2$OTf (90% yield).

Example 6

Synthesis of the Ir(ppz)$_2$(CNtBu)(CCPh)

A solution of fresh LiC≡CPh, prepared by reacting 0.046 mL of phenylacetylene (0.42 mmol) and 0.51 mL of 1.5M hexane nBuLi solution (0.34 mmol) in 20 mL of dry THF at −78° C. for 0.5 hour, was added drop-wise via cannula to a solution of 200 mg of Ir(ppz)$_2$(CNtBu)OTf (0.28 mmol) in 15 mL of dry THF at −78° C. The mixture was reacted for 1 h at −78° C. and the temperature was raised to RT over 2 hours.

0.5 mL of isopropyl alcohol was added and 90% of the solvent was removed under reduced pressure. The solution was diluted with ethyl acetate and washed with water. The organic phase was dried under reduced pressure. The crude material was dissolved in ethyl acetate, filtered to remove insoluble material, and the water precipitated with ethylic ether affording 60 mg of Ir(ppz)$_2$(CNtBu)(CCPh) (32% yield).

LCMS, C18, acetonitrile:H$_2$O, 80:20 to 90:10; ESI+, [M+H]$^+$ 664.4

Example 7

Synthesis of the Ir(ppy)$_2$(CNtBu)(CCPh)

A solution of fresh LiC≡CPh was prepared by reacting 0.057 mL of phenylacetylene (0.525 mmol) and 0.298 mL of 1.5M nBuLi in hexane solution (0.462 mmol) in 15 mL of dry THF at −78° C. for 0.5 hour. The resulting solution was added drop wise via cannula to a solution of 160 mg of Ir(ppy)$_2$(CNtBu)OTf (0.22 mmol) in 10 mL of dry THF at −78° C. The mixture was reacted for 1 h at −78° C. and the temperature was raised to RT over 2 hours. The solvent was removed under reduced pressure and the crude was extracted with diethyl-ether. 67.8 mg of Ir(ppy)$_2$(CNtBu)(CCPh) is obtained (45% yield).

LCMS, C18, acetonitrile:H$_2$O, 80:20 to 90:10; ESI+, [M+H]+ 686.4.

Example 8

Synthesis of the Ir(ppy)$_2$(CNtBu)(CCPhenantr)

A solution of fresh LiC≡CPhenantrene was prepared by reacting 35 mg of 9-ethinyl-phenantrene (0.173 mmol) and 0.125 mL of 1.5M nBuLi hexane solution (0.173 mmol) in 10 mL of dry THF at −78° C. for 0.5 hour. The solution was added drop wise via cannula to a solution of 60 mg of Ir(ppy)$_2$(CNtBu)OTf (0.0785 mmol) in 5 mL of dry THF at −78° C. The mixture was reacted for 1 h at −78° C. and the temperature was raised to RT over 2 hours. The solvent was removed under reduced pressure and the crude was dissolved in diethylether and precipitated with hexane affording 77 mg of Ir(ppy)$_2$(CNtBu)(CCPheneatr) (77% yield).

LCMS, C18, acetonitrile:H$_2$O, 80:20 to 90:10; ESI+, [M+H]$^+$ 786.5.

Example 9

Synthesis of the Ir(ppy)$_2$(CCPh)$_2$Li

A solution of fresh LiC≡CPh was prepared by reacting 0.118 mL of phenylacetylene (1.08 mmol) and 0.48 mL of 1.5M hexane nBuLi solution (0.72 mmol) in 50 mL of dry THF at −78° C. for 0.5 hour. The solution was added drop wise via cannula to a solution of 150 mg of Ir(ppy)$_2$(MeOH)$_2$OTf (0.18 mmol) in 10 mL of dry THF at −78° C. The mixture was reacted for 1 h at −78° C. and the temperature was raised to RT over 2 hours. The solvent was removed under reduced pressure obtaining the Ir(ppy)$_2$(CCPh)$_2$Li.

LCMS, C18, acetonitrile:H$_2$O, 80:20 to 90:10; ESI+−, [Ir(ppy)$_2$(CCPh)$_2$]$^-$=703

Example 10

Synthesis of the Ir(ppz)$_2$(CNtBu)(CCPhenantr)

A solution of fresh LiC≡CPhenantrene prepared by reacting 102.7 mg of 9-Ethinyl-Phenantrene (0.508 mmol) and 0.303 mL of 1.6M hexane nBuLi solution (0.486 mmol) in 10 mL of dry THF at −78° C. for 0.5 hour was added drop wise, via cannula, to a solution of 157 mg of Ir(ppz)$_2$(CNtBu)OTf (0.221 mmol) in 20 mL of dry THF at −78° C. The mixture was reacted for 1 h at −78° C. and the temperature raised to RT over 2 hours.

The solvent was removed under reduced pressure, the crude was dissolved in ethylacetate and the product precipitated with diethylether. The precipitate was washed 3 times with diethyleter/hexane 1/3 v/v obtaining. The organic solution was dried and the solid was washed 3 times with diethyleter/hexane 1/3 v/v. The two precipitate accounts for 140 mg of Ir(ppz)$_2$(CNtBu)(CCPheneatr) (83% yield).

LCMS, C8, acetonitrile:H$_2$O, 80:20; ESI+: [M+H]+ 764.2; [M-(CCPhenantrene)+AcCN]$^+$ 603.2.

Table 1 provides the photophysical properties at room temperature in toluene (tol) or CH$_2$CL$_2$ (DCM) and at 77K in 2MeTHF (77K). Criteria for the reading of the emissions: peak maxima of the shortest wavelength emission.

TABLE 2

| Compound | Emission RT | | | Emission 77K | |
|---|---|---|---|---|---|
| | λ (nm) | Φ PL | τ μs | λ (nm) | τ μs |
| Ir(ppz)$_2$(CNtBu)(CCPh) | — | — | — | 420 | 1460 |
| Ir(ppz)$_2$(CNtBu)(CCPhenantr) | 548 | 0.07(tol) | 442 | 531 | 1758 |
| Ir(ppy)$_2$(CNtBu)(CCPh) | 472 | 0.26(tol) | 0.81(70%) 1.92(30%) | 458 | 4.3(64%) 9.06(36%)$^a$ 4.77$^b$ |
| Ir(ppy)$_2$(CNtBu)(CCPhenantr) | 470 | 0.07(DCM) | 0.52 and 156 | 530 | 1515 |

$^a$lifetime @ 500 nm;
$^b$lifetime @ 460 nm;

Example 11

Devices having the following general devices structure were prepared:
ITO/PVK/CBP(Ir complex 8% w/w)/BCP(400 Å)/LiF(10 Å)/Al The PVK layer was formed by spin coating on a ITO substrate from a 20 mg/mL chlorobenzene solution at 3000 rpm for 40 seconds and annealed at 150° C. for 1 h. The emissive layer was formed using a solution of CBP (with 8% w/w of the Ir complex) spin coated on the PVK layer from a 15 mg/mL chloroform solution (with the proper Ir complex co-dissolved at 8% w/w concentration) at 3000 rpm for 40 sec. No annealing performed was performed for this layer. The BCP, LiF and Al were then vacuum deposited in sequence.

The device data for devices prepared using Ir(ppz)$_2$(CNtBu)(CCPhenantr), Ir(ppy)$_2$(CNtBu)(CCPhenantr), and, as reference, fac-Ir(ppy)$_3$, as the Ir complex are presented in FIGS. 20 to 23.

The invention claimed is:

1. A compound having the formula I:

(I)

wherein: $X^{1\frown}X^2$ is a substituted or unsubstituted bidentate cyclometallated aromatic ligand; $X^1$ and $X^2$ are independently selected from C and N; Z is an acetylide ligand having the structure: —C≡C—R$^1$, —C≡C—(C≡C)$_x$—R$^1$, or —C≡C-(A-C≡C)$_y$—R$^1$, each R$^1$ is independently selected from the group consisting of H, alkyl, cycloalkyl, alkenyl, cycloalkenyl, aryl, heteroaryl, Si(R$^2$)$_3$, M(L)$_z$, and a heterocyclic group, each of which may be substituted or unsubstituted; each x is independently selected from 0-5; each y is independently selected from 0-5; each R$^2$ is independently selected from H, alkyl, cycloalkyl, alkenyl, cycloalkenyl, aryl, heteroaryl, and a heterocyclic group; M is a metal atom; L is a mono-, bi- or tridentate ligand; z is 0-5; A is aryl or heteroaryl; Y is a monodentate ancillary ligand; b is 0, 1, 2, or 3; the sum of a+b+n is 4 or 5; and Cat is an optional cation the charge of which provides a net neutral charge for formula I, wherein n is 2 and a is 2.

2. A compound having the formula I:

(I)

wherein: $X^{1\frown}X^2$ is a substituted or unsubstituted bidentate cyclometallated aromatic ligand; $X^1$ and $X^2$ are independently selected from C and N; Z is an acetylide ligand having the structure: —C≡C—R$^1$, —C≡C—(C≡C)$_x$—R$^1$, or —C≡C-(A-C≡C)$_y$—R$^1$, each R$^1$ is independently selected from the group consisting of H, alkyl, cycloalkyl, alkenyl, cycloalkenyl, aryl, heteroaryl, Si(R$^2$)$_3$, M(L)$_z$, and a heterocyclic group, each of which may be substituted or unsubstituted; each x is independently selected from 0-5; each y is independently selected from 0-5; each R$^2$ is independently selected from H, alkyl, cycloalkyl, alkenyl, cycloalkenyl, aryl, heteroaryl, and a heterocyclic group; M is a metal atom; L is a mono-, bi- or tridentate ligand; z is 0-5; A is aryl or heteroaryl; a is 1; b is 1; n is 2; the sum of a+b+n is 4; and Cat is an optional cation the charge of which provides a net neutral charge for formula I, wherein Y has the formula —C≡N—R$^3$; and R$^3$ is selected from the group consisting of alkyl, cycloalkyl, alkenyl, aryl, aralkyl, and heteroaryl.

3. A compound having the formula III:

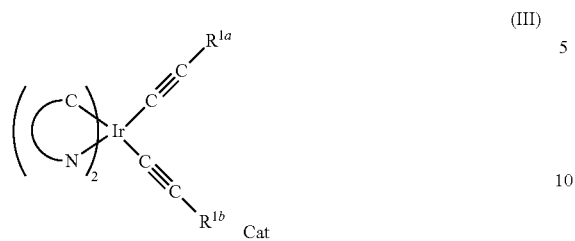

wherein C^N is a substituted or unsubstituted cyclometallated ligand; $R^{1a}$ and $R^{1b}$ are independently selected from the group consisting of H, alkyl, cycloalkyl, alkenyl, cycloalkenyl, aryl, heteroaryl, $Si(R^2)_3$, $M(L)_z$, and a heterocyclic group, each of which may be substituted or unsubstituted; each $R^2$ is independently selected from H, alkyl, cycloalkyl, alkenyl, cycloalkenyl, aryl, heteroaryl, and a heterocyclic group; M is a metal atom; L is a mono-, bi- or tridentate ligand; z is 0-5; and Cat is an optional cation the charge of which provides a net neutral charge for formula III.

* * * * *